United States Patent
Vyakarnam et al.

(10) Patent No.: US 6,306,424 B1
(45) Date of Patent: Oct. 23, 2001

(54) FOAM COMPOSITE FOR THE REPAIR OR REGENERATION OF TISSUE

(75) Inventors: Murty N. Vyakarnam, New York, NY (US); Mark C. Zimmerman, East Brunswick, NJ (US); Angelo George Scopelianos, Whitehouse Station, NJ (US); Iksoo Chun, Flemington, NJ (US); Mora C. Melican, Bridgewater, NJ (US); Clairene A. Bazilio, Plainfield, NJ (US); Mark B. Roller, North Brunswick, NJ (US); David V. Gorky, Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/469,118

(22) Filed: Dec. 21, 1999

Related U.S. Application Data

(63) Continuation-in-part of application No. 09/345,096, filed on Jun. 30, 1999.

(51) Int. Cl.[7] ................................ A61F 2/00; B32B 5/14
(52) U.S. Cl. ..................... 424/426; 428/114; 428/116; 428/118; 428/137; 428/304.4; 428/306.6; 428/308.4; 428/317.9; 428/338; 428/480; 424/422; 424/425; 424/428; 424/486; 623/16; 514/2
(58) Field of Search ...................... 428/114, 116, 428/118, 137, 304.4, 306.6, 308.4, 317.9, 480, 338; 424/422, 425, 426, 428, 486; 623/16; 514/2

(56) References Cited

U.S. PATENT DOCUMENTS

| | | |
|---|---|---|
| 4,186,448 | 2/1980 | Brekke . |
| 4,542,539 | 9/1985 | Rowe, Jr. et al. . |
| 5,133,755 | 7/1992 | Brekke . |
| 5,489,306 | 2/1996 | Gorski . |
| 5,492,697 | 2/1996 | Boyan et al. . |
| 5,514,378 | 5/1996 | Mikos et al. . |
| 5,522,895 | 6/1996 | Mikos . |
| 5,607,474 | 3/1997 | Athanasiou et al. . |
| 5,677,355 | 10/1997 | Shalaby et al. . |
| 5,686,091 | 11/1997 | Leong et al. . |
| 5,711,960 | 1/1998 | Shikinami . |
| 5,716,413 | 2/1998 | Walter et al. . |
| 5,723,508 | 3/1998 | Healy et al. . |
| 5,755,792 | 5/1998 | Brekke . |
| 5,769,899 | 6/1998 | Schwartz et al. . |
| 5,770,193 | 6/1998 | Vacanti et al. . |
| 5,891,558 | 4/1999 | Bell et al. . |

FOREIGN PATENT DOCUMENTS

| | | |
|---|---|---|
| 274898 | 7/1988 | (EP) . |
| WO 00/21470 | 4/2000 | (WO) . |

*Primary Examiner*—Samuel A. Acquah

(57) ABSTRACT

The present patent describes a biocompatible composite made of a first fibrous layer attached to a three-dimensional inter-connected open cell porous foams that have a gradient in composition and/or microstructure through one or more directions. These composites can be made from blends of absorbable and biocompatible polymers. These biocompatible composites are particularly well suited to tissue engineering applications and can be designed to mimic tissue transition or interface zones.

39 Claims, 15 Drawing Sheets

$100 \mu m$

100 μm 1 mm 1 mm

100 μm

100 μm

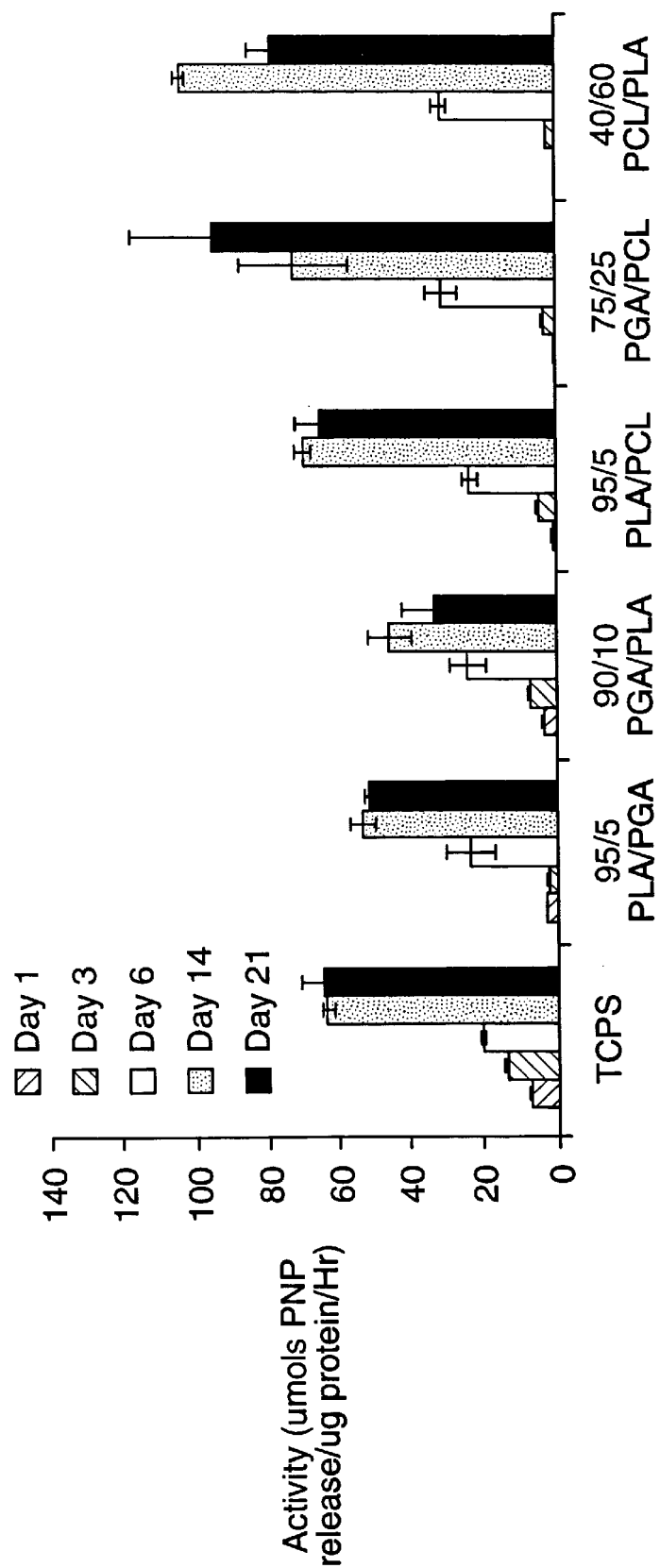

150 μm

150 μm

100 μm

100 μm

10 μm

FOAM COMPOSITE FOR THE REPAIR OR REGENERATION OF TISSUE

This application is a continuation-in-part of application Ser. No. 09/345,096, filed Jun. 30, 1999.

FIELD OF THE INVENTION

The present invention relates generally to the field of tissue repair and regeneration. More particularly the present invention relates to porous biocompatible bioabsorbable foams that have a gradient in composition and/or microstructure that serve as a template for tissue regeneration, repair or augmentation.

BACKGROUND OF THE INVENTION

Open cell porous biocompatible foams have been recognized to have significant potential for use in the repair and regeneration of tissue. Early efforts in tissue repair focused on the use of amorphous biocompatible foam as porous plugs to fill voids in bone. Brekke, et al. (U.S. Pat. No. 4,186,448) described the use of porous mesh plugs composed of polyhydroxy acid polymers such as polylactide for healing bone voids. Several attempts have been made in the recent past to make TE scaffolds using different methods, for example U.S. Pat. Nos. 5,522,895 (Mikos) and 5,514,378 (Mikos, et al.) using leachables; U.S. Pat. Nos. 5,755,792 (Brekke) and 5,133,755 (Brekke) using vacuum foaming techniques; U.S. Pat. Nos. 5,716,413 (Walter, et al.) and 5,607,474 (Athanasiou, et al.) using precipitated polymer gel masses; U.S. Pat. Nos. 5,686,091 (Leong, et al.) and 5,677,355 (Shalaby, et al.) using polymer melts with fugitive compounds that sublimate at temperatures greater than room temperature; and U.S. Pat. Nos. 5,770,193 (Vacanti, et al.) 5,769,899 (Schwartz, et al.) and 5,711,960 (Shikinami) using textile-based fibrous scaffolds. Hinsch et al. (EPA 274,898) described a porous open cell foam of polyhydroxy acids with pore sizes from about 10 to about 200 $\mu$m for the in-growth of blood vessels and cells. The foam described by Hincsh could also be reinforced with fibers, yarns, braids, knitted fabrics, scrims and the like. Hincsh's work also described the use of a variety of polyhydroxy acid polymers and copolymers such as poly-L-lactide, poly-DL-lactide, polyglycolide, and polydioxanone. The Hincsh foams had the advantage of having regular pore sizes and shapes that could be controlled by the processing conditions, solvents selected, and the additives.

However, the above techniques have limitations in producing a scaffold with a gradient structure. Most of the scaffolds are isotropic in form and function and lack the anisotropic features of natural tissues. Further, it is the limitation of prior art to make 3D scaffolds that have the ability to control the spatial distribution of various pore shapes. The process that is described to fabricate the microstructure controlled foams is a low temperature process that offers many advantages over other conventional techniques. For example the process allows the incorporation of thermally sensitive compounds like proteins, drugs and other additives with the thermally and hydrolytically unstable absorbable polymers.

Athanasiou et al. (U.S. Pat. No. 5,607,474) have more recently proposed using a two layer foam device for repairing osteochondral defects at a location where two dissimilar types of tissue are present. The Athanasiou device is composed of a first and second layer, prepared in part separately, and joined together at a subsequent step. Each of the scaffold layers is designed to have stiffness and compressibility corresponding to the respective cartilage and bone tissue. Since cartilage and bone often form adjacent layers in the body this approach is an attempt to more clearly mimic the structure of the human body. However, the interface between the cartilage and bone in the human body is not a discrete junction of two dissimilar materials with an abrupt change in anatomical features and/or the mechanical properties. The cartilage cells have distinctly different cell morphology and orientation depending on the location of the cartilage cell in relation to the underlying bone structure. The difference in cartilage cell morphology and orientation provides a continuous transition from the outer surface of the cartilage to the underlying bone cartilage interface. Thus the two layer system of Athanasiou, although an incremental improvement, does not mimic the tissue interfaces present in the human body.

Another approach to make three-dimensional laminated foams is proposed by Mikos et al. (U.S. Pat. No. 5,514,378). In this technique which is quite cumbersome, a porous membrane is first prepared by drying a polymer solution containing leachable salt crystals. A three-dimensional structure is then obtained by laminating several membranes together, which are cut to a contour drawing of the desired shape.

One of the major weaknesses of the prior art regarding three-dimensional porous scaffolds used for the regeneration of biological tissue like cartilage is that their microstructure is random. These scaffolds, unlike natural tissue, do not vary in morphology or structure. Further, current scaffolds do not provide adequate nutrient and fluid transport for many applications. Finally, the laminated structures are not completely integrated and subjected to delamination under in vivo conditions.

Therefore, it is an object of the present invention to provide a biocompatible, bioabsorbable foam that provides a continuous transitional gradient of morphological, structural and/or materials. Further, it is preferred that foams used in tissue engineering have a structure that provides organization at the microstructure level that provides a template that facilitates cellular invasion, proliferation and differentiation that will ultimately result in regeneration of functional tissue.

SUMMARY OF INVENTION

The present invention provides a composite comprising a first layer that is a biocompatible filamentous layer and a second layer of biocompatible foam. This composite structure allows for the creation of structures with unique mechanical properties. The fibrous layer allows the composite to have variable mechanical strength depending on the design, a different bioabsorption profile, and a different microenvironment for cell invasion and seeding, which are advantageous in a variety of medical applications. The fibrous layer may be made from a variety of biocompatible polymers and blends of biocompatible polymers, which are preferably bioabsorbable. The biocompatible foam may be either a gradient foam or a channeled foam. The gradient foam has a substantially continuous transition in at least one characteristic selected from the group consisting of composition, stiffness, flexibility, bioabsorption rate, pore architecture and/or microstructure. The gradient foam can be made from a blend of absorbable polymers that form compositional gradient transitions from one polymeric material to a second polymeric material. In situations where a single chemical composition is sufficient for the application, the invention provides a composite that may have microstructural variations in the structure across one or more dimensions that may mimic the anatomical features of the tissue (e.g. cartilage, skin, bone etc.). The channeled foam provides channels that extend through the foam to facilitate cell migration and nutrient flow throughout the channeled foam.

The present invention also provides a method for the repair or regeneration of tissue contacting a first tissue with the composite described above at a location on the composite that has appropriate properties to facilitate the growth of said tissue. These composite structures are particularly useful for the regeneration of tissue between two or more different types of tissues. For a multi-cellular system in the simplest case, one cell type could be present on one side of the scaffold and a second cell type on the other side of the scaffold. Examples of such regeneration can be (a) vascular tissue: with smooth muscle on the outside and endothelial cells on the inside to regenerate vascular structures; (b) meniscal tissue: by implanting with chondrocytes inside foam of the composite and orienting the fibrous surface to the outside.

BRIEF DESCRIPTION OF FIGURES

FIG. 9A shows the porosity of the surface of the scaffold that preferably would face the wound bed. FIG. 9B shows the porosity of the surface of the scaffolding that would preferably face away from the wound bed. FIG. 9C shows a cross section of the scaffold with channels running through the thickness of the foam.

DETAILED DESCRIPTION OF THE INVENTION

Figure 1:
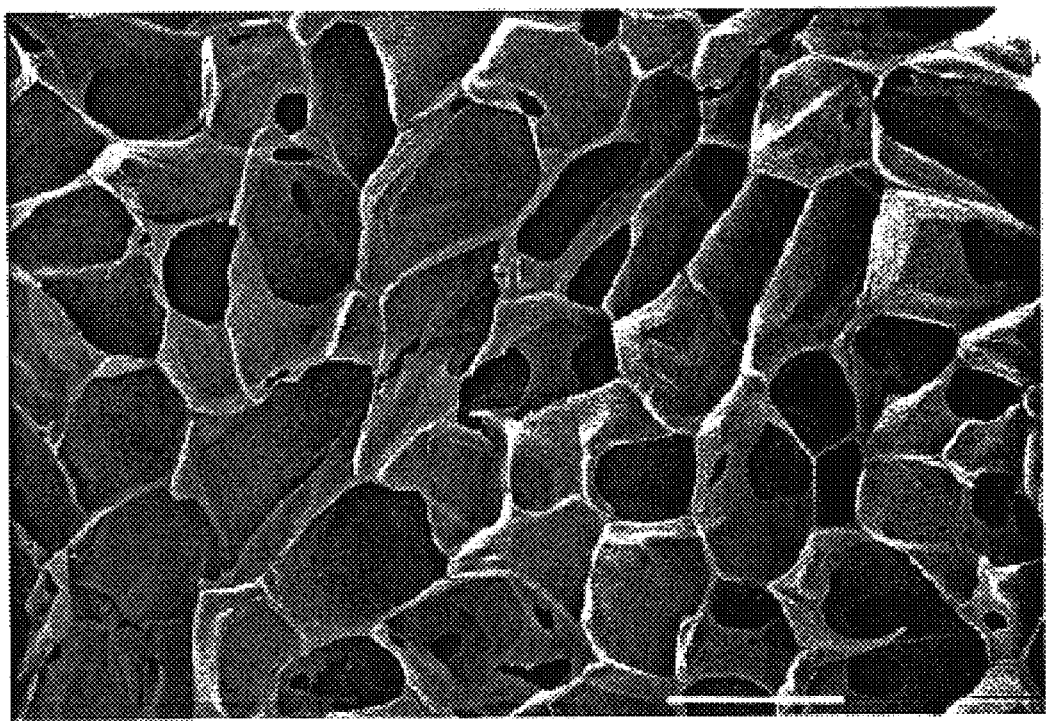
FIG. 1 is a scanning electron micrograph of the cross section of a random microstructure foam made from 5% solution of 35/65 ε-caprolactone-co-glycolide copolymer.

This invention describes porous bioabsorbable polymer foams that have novel microstructures. The features of such foams can be controlled to suit a desired application by choosing the appropriate conditions to form the foam during lyophilization. These features in absorbable polymers have distinct advantages over the prior art where the scaffolds are typically isotropic or random structures. However, it is preferred that foams used in tissue engineering (i.e. repair or regeneration) have a structure that provides organization at the microstructural level that provides a template that facilitates cellular organization and regeneration of tissue that has the anatomical, biomechanical, and biochemical features of normal tissues. These foams can be used to repair or regenerate tissue (including organs) in animals such as domestic animals, primates and humans.

The features of such foams can be controlled to suit desired application by selecting the appropriate conditions for lyophilization to obtain one or more of the following properties: (1) interconnecting pores of sizes ranging from about 10 to about 200 μm (or greater) that provide pathways for cellular ingrowth and nutrient diffusion; (2) a variety of porosities ranging from about 20% to about 98% and preferably ranging from about 80% to about 95%; (3) gradient in the pore size across one direction for preferential cell culturing; (4) channels that run through the foam for improved cell invasion, vascularization and nutrient diffusion; (5) micro-patterning of pores on the surface for cellular organization; (6) tailorability of pore shape and/or orientation (e.g. substantially spherical, ellipsoidal, columnar); (7) anisotropic mechanical properties; (8) composite foams with a polymer composition gradient to elicit or take advantage of different cell response to different materials; (9) blends of different polymer compositions to create structures that have portions that will break down at different rates; (10) foams co-lyophilized or coated with pharmaceutically active compounds including but not limited to biological factors such as RGD's, growth factors (PDGF, TGF-β, VEGF, BMP, FGF etc.) and the like; (11) ability to make 3 dimensional shapes and devices with preferred microstructures; and (12) lyophilization with other parts or medical devices to provide a composite structure. These controlled features in absorbable polymers have distinct advantages over the prior art where the scaffolds are typically isotropic or random structures with no preferred morphology at the pore level. However, it is preferred that foams used in tissue scaffolds have a structure that provides organization at the microstructure level and provides a template that facilitates cellular organization that may mimic natural tissue. The cells will adhere, proliferate and differentiate along and through the contours of the structure. This will ultimately result in a cultured tissue that may mimic the anatomical features of real tissues to a large extent.

Figure 2:
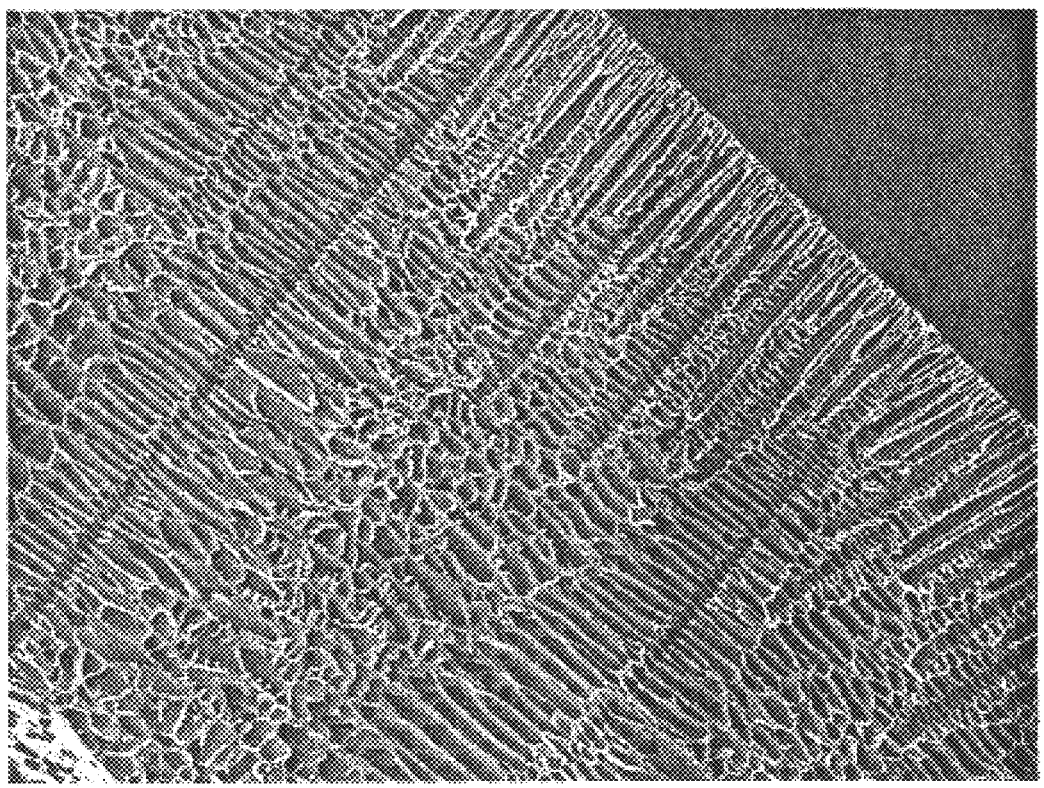
FIG. 2 is a scanning electron micrograph of the cross section of a foam with vertical open channels made from 10% solution of 35/65 ε-caprolactone-co-glycolide copolymer.
Figure 3:
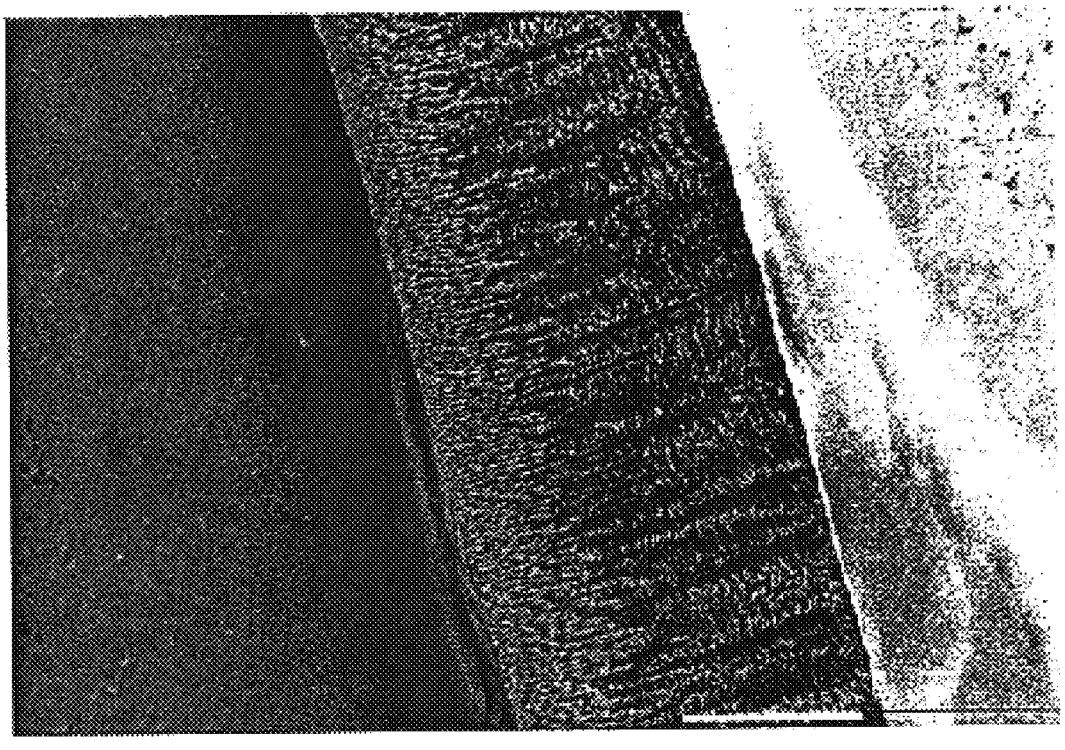
FIG. 3 is a scanning electron micrograph of the cross section of a foam with architectural gradient made from 10% solution of 35/65 ε-caprolactone-co-glycolide copolymer.

For example, as shown in FIG. 3 the orientation of the major axis of the pores may be changed from being in the same plane as the foam to being oriented perpendicular to the plane of the foam. As can be seen from FIG. 3 the pore size can be varied from a small pore size generally between about 30 μm and about 50 μm to a larger size of from about 100 μm to about 200 μm in porous gradient foams. Ideally the foam structure could be created to facilitate the repair or regeneration of human tissue junctions such as the cartilage to bone junction present in joints. This foam would progress from a small (i.e. about 30 μm to about 150 μm in diameter) round pores to larger column-like pores (i.e. about 30 μm to about 400 μm in diameter, preferably about 100 μm to about 400 μm in diameter, in most cases with a length to diameter ratio of at least 2). Foams with channels are illustrated in FIG. 2 and FIG. 3.

The channels formed by this process generally begin on one surface of the foam and may traverse the thickness of the foam. The channel's length is generally at least two times the average pore diameter and preferably are at least four times the average pore diameter and most preferably at least eight times the average pore diameter. Channels for most applications will be at least 200 microns in length and may extend through the thickness of the foam. The diameter of the channel will be at least one time the size of the average pore diameter and preferably at least 2 to 3 times the average pore diameter. The channel size and diameter of course will be selected based on the desired functionality of the channel such as cellular invasion, nutrient diffusion or as an avenue for vascularization.

There are a number of biological tissues that demonstrate gradient architectures. Examples of tissues where a gradient scaffold could be used, include, but are not limited to: bone, spine disc, articular cartilage, meniscus, fibrocartilage, tendons, ligaments, dura, skin, vascular grafts, nerves, liver, and pancreas. The examples below only highlight a few tissues where gradient scaffolds could be used. The design of tissue engineered scaffolds to facilitate development of these organ structures would benefit greatly from the ability to process or create a gradient architecture in the scaffold.

Cartilage

Figure 8:
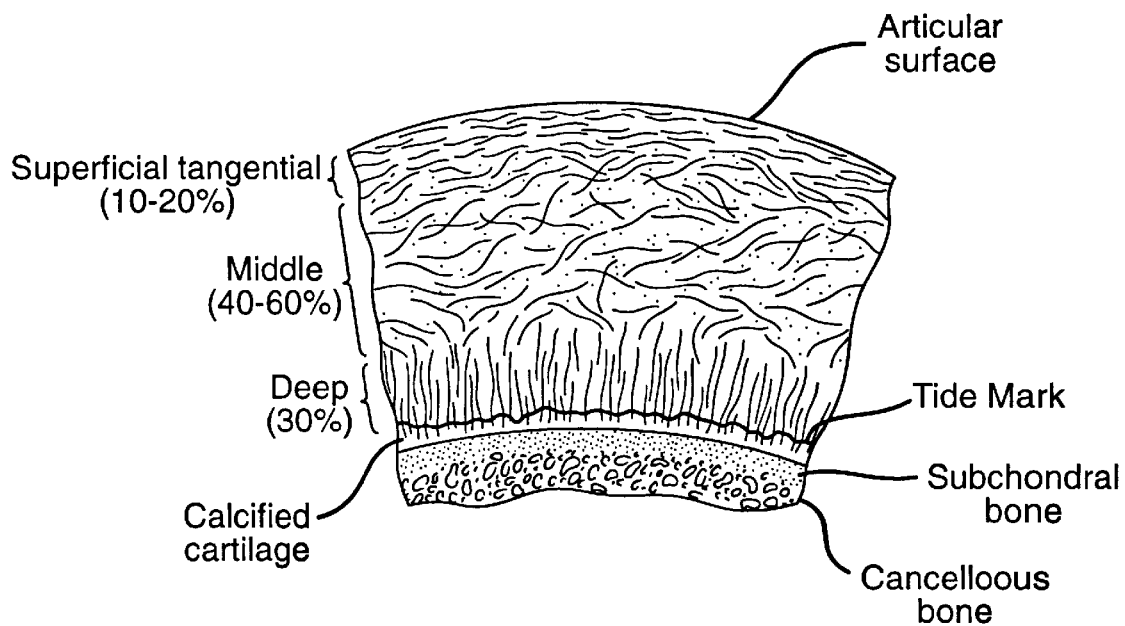
FIG. 8 is an anatomical sketch of cartilage tissue.

Articular cartilage covers the ends of all bones that form articulating joints in humans and animals. The cartilage acts in the joint as a mechanism for force distribution and as a bearing surface between different bones. Without articular cartilage, stress concentration and friction would occur to the degree that the joint would not permit ease of motion. Loss of the articular cartilage usually leads to painful arthritis and decreased joint motion. A schematic showing the morphological features of a healthy cartilage is shown in FIG. 8.

Articular cartilage is an excellent example of a naturally occurring gradient structure. Articular cartilage is composed of four different zones that include the superficial or tangential zone within the first 10–20% of the structure (this includes the articular surface), the middle zone which is 40–60% of the middle structure, and the deep zone that is adjacent to the tide mark, and a transition zone between the bone and cartilage that is composed of calcified cartilage. Subchondral bone is located adjacent to the tide mark and this transitions into cancellous bone. In the superficial or tangential zone, the collagen fibrils are parallel to the surface. The fibers are oriented to resist shear forces generated during normal joint articulation. The middle zone has a randomly arranged organization of much larger diameter collagen fibers. Finally, in the deep zone there are larger collagen fiber bundles, which are perpendicular to the surface, and they insert into the calcified cartilage. The cells are speroidiol and tend to arrange themselves in a columnar manner. The calcified cartilage zone has smaller cells with relatively little cytoplasm.

A preferred embodiment of this invention would be to generate a gradient foam structure that could act as a template for multiple distinct zones. These foam structures could be fabricated in a variety of shapes to regenerate or repair osteochondral defects and cartilage. One potential foam structure would be cylindrical in shape with an approximate dimensions of 10 mm in diameter and 10 mm in depth. The top surface is would be approximately 1 mm thick and would be a low porosity layer to control the fluid permeability. By adopting a suitable processing method the surface porosity of the foam could be controlled. The porosity of this skin like surface can be varied from completely impervious to completely porous. Fluid permeability would be controlled by surface porosity. Below such a skin the structure would consist of three zones. An upper porous zone which lies adjacent to cartilage tissue, a lower porous zone which lies adjacent to bone tissue, and a transition zone between the upper and lower porous zones. For articular cartilage, it is currently preferred that the stiffness (modulus) of the upper and lower porous layers at the time of implantation be at least as stiff, as the corresponding adjacent tissue. In such a case the porous layers will be able to support the environmental loading and thereby protect the invading cells until they have differentiated and consolidated into tissue that is capable of sustaining load. For example the porous structure used for the superficial tangential zone could have elongated pores and the orientation of the structure could be parallel to the surface of the host cartilage. However, the deep zone may have a porosity of about 80 to about 95% with pores that are of the order of 100 μm (about 80 μm to about 120 μm). It is expected that chondrocytes will invade this zone. Below this, would be a zone with larger pores (about 100 μm to about 200 μm) and a porosity in the range of about 50 to about 80%. Such 100 μm to about 200 μm porous foam would have a structure such that the struts or walls of the pores are larger and vertical to the load, similar to the naturally occurring structure and to bear the loads. Finally, at the bottom of this structure there is a need for larger pores (about 150 μm to about 300 μm) with higher stiffness to be structurally compatible with cancellous bone. The foam in this section could be reinforced with ceramic particles or fibers made up of calcium phosphates and the like.

Recent data generated in our laboratories support the hypothesis that cell invasion can be controlled by pore size. In these studies, a scaffold made of 95/5 mole percent poly(L)lactide-co-ε-caprolactone) with an approximate pore size of about 80 μm had chondrocyte invasion of about 30 cells/mm$^2$ of the scaffold (under static conditions). Scaffolds made of 40/60 mole percent poly(ε-caprolactone-co-(L) lactide) with a larger approximate pore size of about 100 μm had a statistically significantly greater cellular invasion of 50 cells/mm$^2$ (under static conditions). In both cases the cells were bovine chondrocytes. A very simple gradient structure with a variation of pore sized from about 80 μm to about 150 μm would provide a structure where chondrocytes would more easily invade the area with larger pores. The area with smaller pores would be void of chondrocytes or would be filled with a second cell types (e.g., fibroblasts).

In a compositionally gradient foam a blend of two or more elastomeric copolymers or in combination with high modulus semi-crystalline polymers along with additives such as growth factors or particulates can be chosen such that first a desired pore gradient is developed with a preferred spatial organization of the additives. Then using a variety of the approaches referred to in the preferred methods of making gradient foams, a compositional gradient can be superimposed primarily due to the differences in the polymer-solvent phase separation behavior of each system. Such a gradient foam structure would elicit a favorable response to chondrocytes or osteoblasts depending on the spatial location.

Further, the purpose of a functional gradient is to more evenly distribute the stresses across a region through which mechanical and/or physical properties are varying and thereby alleviate the stress concentrating effects of a sudden interface. This more closely resembles the actual biological tissues and structures, where structural transitions between differing tissues such as cartilage and bone are gradual. Therefore, it is an object of the present invention to provide an implant with a functional gradient between material phases. The present invention provides a multi-phasic functionally graded bioabsorbable implant with attachment means for use in surgical repair of osteochondral defects or sites of osteoarthritis. Several patents have proposed systems for repairing cartilage that could be used with the present inventive porous scaffolds. For example, U.S. Pat. No. 5,769,899 describes a device for repairing cartilage defects and U.S. Pat. No. 5,713,374 describes securing cartilage repair devices with bone anchors (both hereby incorporated herein by reference).

Bone

Gradient structures naturally occur for the bone/cartilage interface. In a study in our laboratories, we have demonstrated that material differences significantly influence cell function. In initial and long-term response of primary osteoblasts to polymer films (95/5 L-lactide-co-glycolide copolymer, 90/10 glycolide-co-(L)lactide copolymer, 95/5 L-lactide-co-$\epsilon$-caprolactone copolymer, 75/25 glycolide-co-(L)lactide copolymer and 40/60 $\epsilon$-caprolactone-co-(L) lactide copolymer and knitted meshes (95/5 (L)lactide-co-glycolide and 90/10 glycolide-co-(L)lactide copolymers) were evaluated in vitro. The results demonstrated that osteoblasts attached and proliferated well on all the biodegradable polymer films and meshes following 6-day incubation. None of the tested polymer films, except a 40/60 $\epsilon$-caprolactone-co-(L)lactide copolymer film, demonstrated significant enhancement in differentiation of primary rat osteoblasts as compared to tissue culture polystyrene (control). Films made of 40/60 caprolactone-co-(L)lactide promoted enhanced differentiation of cultured osteoblasts as demonstrated by increased alkaline phosphatase activity and osteoclacin mRNA expression as compared to the other films and TCPS. Hence, it is clear that different absorbable materials will significantly alter cell function and differentiation. By identifying the optimal materials for cell growth and differentiation a composite materials with a gradient composition could be utilized to optimize tissue regeneration with different cell types in the same scaffold.

Therefore, for bone repair or regeneration devices or scaffoldings, a device made from a homopolymer, copolymer (random, block, segmented block, tappered blocks, graft, triblock,.etc.) having a linear, branched or star structure containing $\epsilon$-caprolactone is especially preferred. Currently preferred are aliphatic polyester copolymers containing in the range of from about 30 weight percent to about 99 weight percent $\epsilon$-caprolactone. Suitable repeating units that may be copolymerized with $\epsilon$-caprolactone are well known in the art. Suitable comonomers that may be copolymerized with $\epsilon$-caprolactone include , but are not limited to lactic acid, lactide (including L-, D-, meso and D, L mixtures), glycolic acid, glycolide, p-dioxanone (1,4-dioxan-2-one), trimethylene carbonate (1,3-dioxan-2-one), $\delta$-valerolactone, $\beta$-butyrolactone, $\epsilon$-decalactone, 2,5-diketomorpholine, pivalolactone, $\alpha,\alpha$-diethylpropiolactone, ethylene carbonate, ethylene oxalate, 3-methyl-1,4-dioxane-2,5-dione, 3,3-diethyl-1,4-dioxan-2,5-dione, $\gamma$-butyrolactone, 1,4-dioxepan-2-one, 1,5-dioxepan-2-one, 6,6-dimethyl-dioxepan-2-one, 6,8-dioxabicycloctane-7-one and combinations thereof.

Preferred medical devices or tissue scaffoldings for bone tissue repair and/or regeneration containing bioabsorbable polymers made from $\epsilon$-caprolactone include but are not limited to the porous foam scaffoldings (such as described in this application), fibrous three dimensional, spun, nonwoven, woven, knitted, or braided tissue scaffoldings, composite containing reinforcing fibers, matrices and combinations thereof.

Skin

Another example of a tissue that has a gradient structure is skin. The basic structure of skin has two distinct, but well integrated layers where the thickness of each layer varies at different locations of the body. The outer layer or epidermis, is avascular and mainly consists of keratinocytes with smaller numbers of immune cells (Langerhan cells) and pigmented cells (melanocytes). The keratinocytes produce keratin fibers and corneocyte envelopes, which gives the epidermis its durability and protective capabilities. The development of these structures is completely dependent upon the differentiation state of the epidermis. The epidermis forms a stratified epithelium, with different protein expression patterns, as the cells move further away from the basement membrane. This stratified layer of differentially expressing cells must be formed for maintenance of epidermal function. Below the epidermis is the dermis, which is a dense irregular connective tissue that is highly vascular. This layer is heavily populated with collageneic and elastic fibers, which give it its exceptional elasticity and strength. Fibroblasts are the main cell types in this layer. Between these two layers is the basement membrane, which serves as the site of attachment for epidermal cells and serves also to regulate their function and differentiation. The layer of keratinocytes, which attaches directly to the basement membrane, are cuboidal in shape and highly aligned. This attachment and architecture are critical requirements driving the ultimate production of the higher squamous structures in the epidermis. The basal layer provides a source of precursor cells for repair and replacement of the epidermis. The squamous layers provide strength and resistance to insult and infection.

Figure 9A:
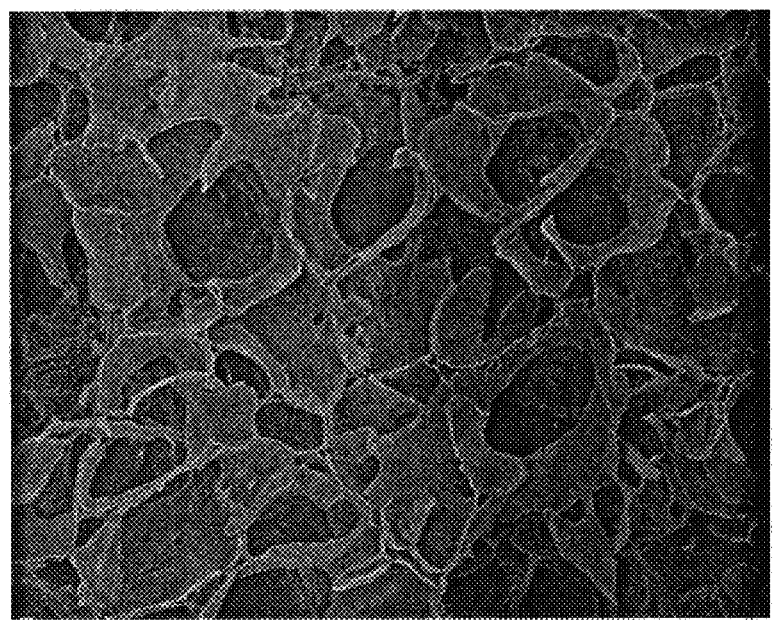
FIGS. 9A, 9B, and 9C are scanning electron micrographs of a 0.5 mm foam made from a 50/50 blend of a 35/65 ε-caprolactone-co-glycolide copolymer and a 40/60 ε-caprolactone-co-(L)lactide copolymer with architecture suitable for use as a skin scaffold.
Figure 9B:
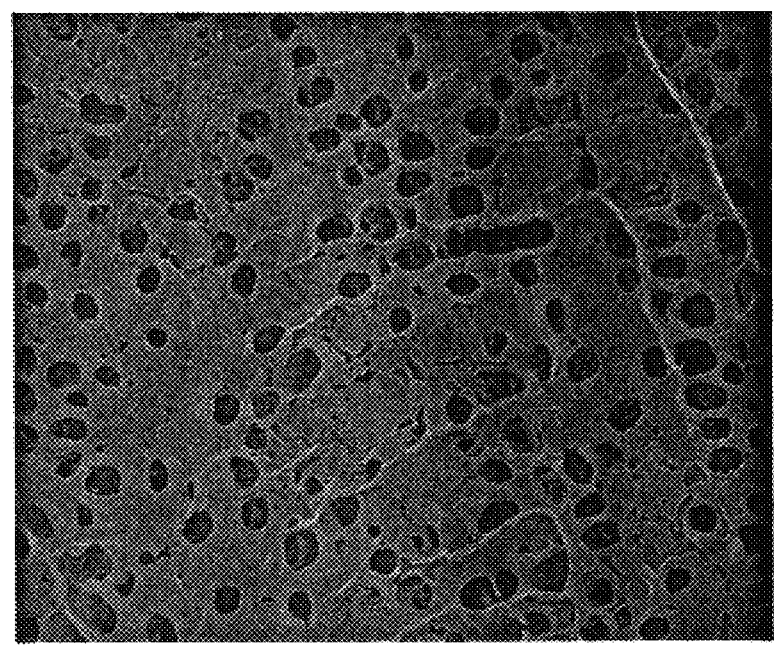
Figure 9C:
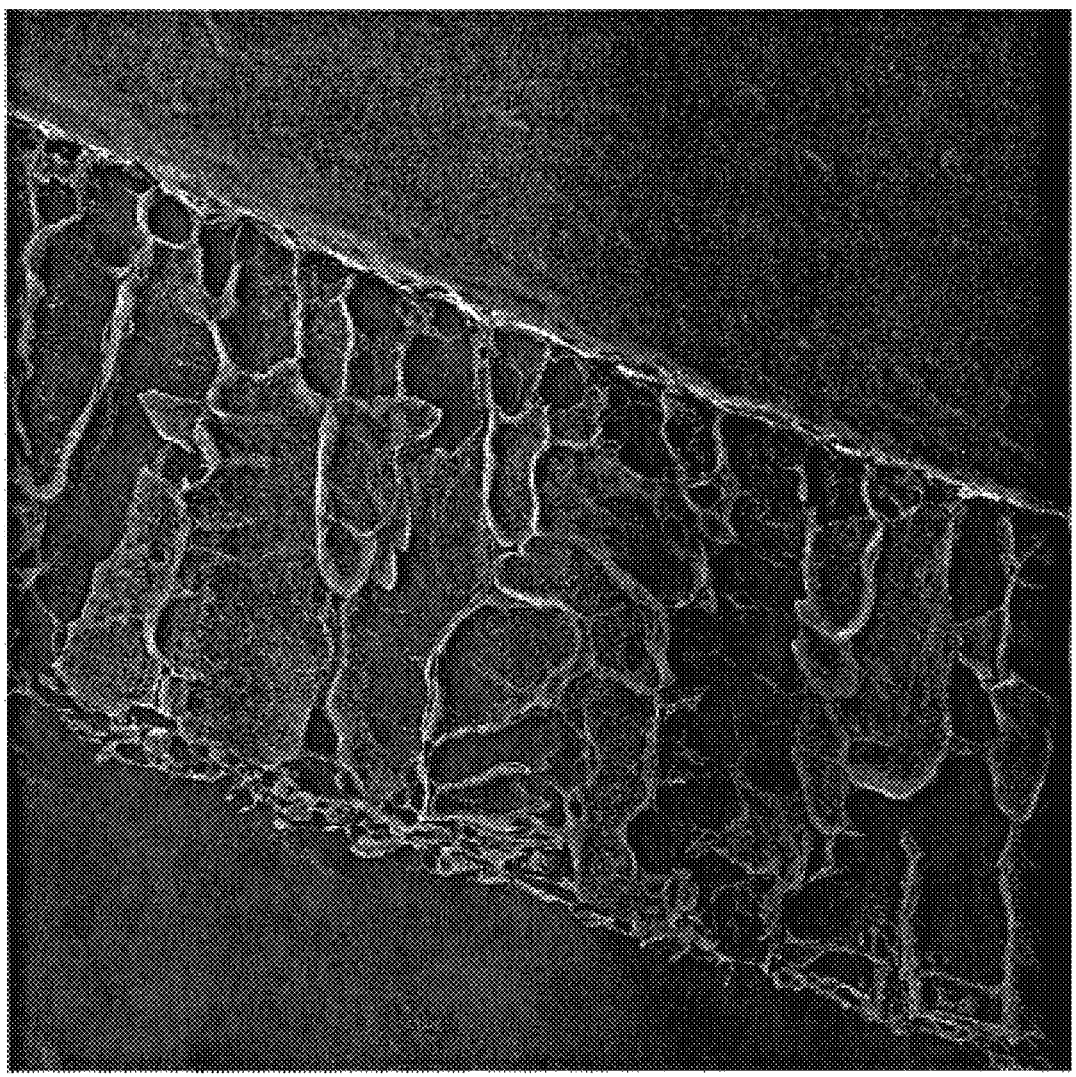
Figure 10:
FIG. 10 is a dark field 40× photomicrograph of a trichrome stained sample illustrating the cellular invasion of the foam shown in FIG. 9, eight days after implantation in a swine model.

Any material used for replacement of skin must be able to entice invasion of fibroblasts or other cells necessary to produce the dermal components of the healed tissue. Additionally, the material must not inhibit, and preferably should enhance, the rate of re-epithelialization in such a fashion that a discreet, epidermal basal layer is formed. Materials that permit invasion into the scaffold by migrating keratinocytes can produce partially differentiated cells. Consequently, control of access of particular cell types and a porous design that facilitates the regeneration of the natural tissue can have functional benefits. Now refer to FIGS. 9A, 9B and 9C which illustrates the microstructure of this foam scaffold. FIGS. 10 (100× magnification) and 11 (40× magnification composite picture) provide photomicrographic evidence of the invasion of fibroblasts, macrophages, macrophage giant cells and endothelial-like cells into the a 0.5 mm foam.

The foam tissue scaffolding 101 shown in both pictures was a 50:50 blend of $\epsilon$-caprolactone-co-glycolide copolymer and ε-caprolactone-co-lactide copolymer (made as described in Example 7). The pictures were taken at 8 days after implantation in 1.5 cm×1.5 cm×0.2 cm excisional wound model in a Yorkshire pig model. Complete incorporation of the matrix into the granulation tissue bed is evident in both pictures. The dense fibrous tissue above the foam tissue scaffolding appears to provide a suitable substrate for the over growth of epidermis. PDGF was incorporated into the foam tissue scaffolding shown in FIG. 11. In compromised wound healing models the addition of a growth factor such as PDGF may in fact be necessary.

From our initial studies it appears that it is desirable to use as a skin scaffold a foam tissue scaffold having a thickness of from about 150 μm to about 3 mm, preferably the thickness of the foam may be in the range of from about 300 μm to about 1500 μm and most preferably about 500 to about 1000 μm. Clearly different skin injuries (i.e. diabetic ulcers, venous stasis ulcers, decubitis ulcers, burns etc.) may require different foam thickness. Additionally, the patient's condition may necessitate the incorporation of growth factors, antibiotics and antifungal compounds to facilitate wound healing.

Vascular grafts

The creation of tubular structures with gradients may also be of interest. In vascular grafts, having a tube with pores in the outer diameter which transitions to smaller pores on the inner surface or visa versa may be useful in the culturing of endothelial cells and smooth muscle cells for the tissue culturing of vessels.

Multilayered tubular structures allow the regeneration of tissue that mimics the mechanical and/or biological characteristics of blood vessels will have utility as a vascular grafts. Concentric layers, made from different compositions under different processing conditions could have tailored mechanical properties, bioabsorption properties, and tissue ingrowth rates. The inner most, or luminal layer would be optimized for endothelialization through control of the porosity of the surface and the possible addition of a surface treatment. The outermost, or adventitial layer of the vascular graft would be tailored to induce tissue ingrowth, again by optimizing the porosity (percent porosity, pore size, pore shape and pore size distribution) and by incorporating bioactive factors, pharmaceutical agents, or cells. There may or may not be a barrier layer with low porosity between these two porous layers to increase strength and decrease leakage.

Composition of foams

A variety of absorbable polymers can be used to make foams. Examples of suitable biocompatible, bioabsorbable polymers that could be used include polymers selected from the group consisting of aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amine groups, poly(anhydrides), polyphosphazenes, biomolecules (i.e. biopolymers such as collagen, elastin, bioabsorbable starches, ect.) and blends thereof. For the purpose of this invention aliphatic polyesters include but are not limited to homopolymers and copolymers of lactide (which includes lactic acid, D-,L- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate (repeating units), hydroxyvalerate (repeating units), 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, alpha,alpha-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly (iminocarbonate) for the purpose of this invention include as described by Kemnitzer and Kohn, in the *Handbook of Biodegradable Polymers*, edited by Domb, Kost and Wisemen, Hardwood Academic Press, 1997, pages 251–272. Copoly(ether-esters) for the purpose of this invention include those copolyester-ethers described in "Journal of Biomaterials Research", Vol. 22, pages 993–1009, 1988 by Cohn and Younes and Cohn, Polymer Preprints (ACS Division of Polymer Chemistry) Vol. 30(1), page 498, 1989 (e.g. PEO/PLA). Polyalkylene oxalates for the purpose of this invention include U.S. Pat. Nos. 4,208,511; 4,141,087; 4,130,639; 4,140,678; 4,105,034; and 4,205,399 (incorporated by reference herein). Polyphosphazenes, co-, ter- and higher order mixed monomer based polymers made from L-lactide, D,L-lactide, lactic acid, glycolide, glycolic acid, para-dioxanone, trimethylene carbonate and ε-caprolactone such as are described by Allcock in *The Encyclopedia of Polymer Science*, Vol. 13, pages 31–41, Wiley Intersciences, John Wiley & Sons, 1988 and by Vandorpe, Schacht, Dejardin and Lemmouchi in the *Handbook of Biodegradable Polymers*, edited by Domb, Kost and Wisemen, Hardwood Academic Press, 1997, pages 161–182 (which are hereby incorporated by reference herein). Polyanhydrides from diacids of the form HOOC—$C_6H_4$—O—$(CH_2)_m$—O—$C_6H_4$—COOH where m is an integer in the range of from 2 to 8 and copolymers thereof with aliphatic alpha-omega diacids of up to 12 carbons.

Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150 (which are incorporated herein by reference). Polyorthoesters such as those described by Heller in *Handbook of Biodegradable Polymers*, edited by Domb, Kost and Wisemen, Hardwood Academic Press, 1997, pages 99–118 (hereby incorporated herein by reference).

Currently aliphatic polyesters are the absorbable polymers that are preferred for making gradient foams. Aliphatic polyesters can be homopolymers, copolymers (random, block, segmented, tappered blocks, graft, triblock,etc.) having a linear, branched or star structure. Preferred are linear copolymers. Suitable monomers for making aliphatic homopolymers and copolymers may be selected from the group consisting of, but are not limited, to lactic acid, lactide (including L-, D-, meso and D,L mixtures), glycolic acid, glycolide, ε-caprolactone, p-dioxanone (1,4-dioxan-2-one), trimethylene carbonate (1,3-dioxan-2-one), delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof.

Elastomeric copolymers also are particularly useful in the present invention. Suitable bioabsorbable biocompatible elastomers include but are not limited to those selected from the group consisting of elastomeric copolymers of ε-caprolactone and glycolide (preferably having a mole ratio of ε-caprolactone to glycolide of from about 35:65 to about 65:35, more preferably from 45:55 to 35:65) elastomeric copolymers of ε-caprolactone and lactide, including L-lactide, D-lactide blends thereof or lactic acid copolymers (preferably having a mole ratio of ε-caprolactone to lactide of from about 35:65 to about 65:35 and more preferably from 45:55 to 30:70 or from about 95:5 to about 85:15) elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40) elastomeric copolymers of ε-caprolactone and p-dioxanone (preferably having a mole ratio of ε-caprolactone to p-dioxanone of from about from 30:70 to about 70:30) elastomeric copolymers of p-dioxanone and trimethylene carbonate (preferably having a mole ratio of p-dioxanone to trimethylene carbonate of from about 30:70 to about 70:30), elastomeric copolymers of trimethylene carbonate and glycolide (preferably having a mole ratio of trimethylene carbonate to glycolide of from about 30:70 to about 70:30), elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. Examples of suitable bioabsorbable elastomers are described in U.S. Pat. Nos. 4,045,418; 4,057,537 and 5,468,253 all hereby incorporated by reference. These elastomeric polymers will have an inherent viscosity of from about 1.2 dL/g to about 4 dL/g, preferably an inherent viscosity of from about 1.2 dL/g to about 2 dL/g and most preferably an inherent viscosity of from about 1.4 dL/g to about 2 dL/g as determined at 25° C. in a 0.1 gram per deciliter (g/dL) solution of polymer in hexafluoroisopropanol (HFIP).

Preferably, the elastomers will exhibit a high percent elongation and a low modulus, while possessing good tensile strength and good recovery characteristics. In the preferred embodiments of this invention, the elastomer from which the foams are formed will exhibit a percent elongation greater than about 200 percent and preferably greater than about 500 percent. There properties, which measure the degree of elasticity of the bioabsorbable elastomer, are achieved while maintaining a tensile strength greater than about 500 psi, preferably greater than about 1,000 psi, and a tear strength of greater than about 50 lbs/inch, preferably greater than about 80 lbs/inch.

The polymer or copolymer suitable for forming a gradient foam for tissue regeneration depends on several factors. The chemical composition, spatial distribution of the constituents, the molecular weight of the polymer and the degree of crystallinity all dictate to some extent the in-vitro and in-vivo behavior of the polymer. However, the selection of the polymers to make gradient foams for tissue regeneration largely depends on (but not limited to) the following factors: (a) bio-absorption (or bio-degradation) kinetics; (b) in-vivo mechanical performance; and (c) cell response to the material in terms of cell attachment, proliferation, migration and differentiation and (d) biocompatibility.

The ability of the material substrate to resorb in a timely fashion in the body environment is critical. But the differences in the absorption time under in-vivo conditions can also be the basis for combining two different copolymers. For example a copolymer of 35:65 ε-caprolactone and glycolide (a relatively fast absorbing polymer) is blended with 40:60 ε-caprolactone and (L)lactide copolymer (a relatively slow absorbing polymer) to form a foam. Such a foam could have several different physical structures depending upon the processing technique used. The two constituents can be either randomly inter-connected bicontinuous phases, or the constituents can have a gradient through the thickness or a laminate type composite with a well integrated interface between the two constituent layers. The microstructure of these foams can be optimized to regenerate or repair the desired anatomical features of the tissue that is being engineered.

One preferred embodiment of the present invention is to use polymer blends to form structures which transition from one composition to another composition in a gradient like architecture. Foams having this gradient architecture are particularly advantageous in tissue engineering applications to repair or regenerate the structure of naturally occurring tissue such as cartilage (articular, meniscal, septal, tracheal etc.), esophaguses, skin, bone and vascular tissue. For example by blending an elastomer of ε-caprolactone-co-glycolide with ε-caprolactone-co-lactide (i.e. with a mole ratio of about 5:95) a foam may be formed that transitions from a softer spongy foam to a stiffer more rigid foam similar to the transition from cartilage to bone. Clearly other polymer blends may be used for similar gradient effects or to provide different gradients such as different absorption profiles, stress response profiles, or different degrees of elasticity. Additionally, these foams can be used for organ repair replacement or regeneration strategies that may benefit from these unique scaffolds, including but are not limited to, spine disc, dura, nerve tissue, liver, pancreas, kidney, bladder, tendons, ligaments and breast tissues.

These elastomeric polymers may be foamed by lyophilization, supercritical solvent foaming (i.e., as described in EP 464,163 B1), gas injection extrusion, gas injection molding or casting with an extractable material (i.e., salts, sugar or any other means known to those skilled in the art). Currently it is preferred to prepare bioabsorbable, biocompatible elastomeric foams by lyophilization. Suitable methods for lyophilizing elastomeric polymers to form foams is described in the Examples and in the copending patent application entitled, "Process for Manufacturing Biomedical Foams", assigned to Ethicon, Inc., docket number ETH-1352, filed Jun. 30, 1999 hereby incorporated herein by reference herein.

The foams that are made in this invention are made by a polymer-solvent phase separation technique with modifications to the prior art that unexpectedly creates gradients in the foam structure. Generally, a polymer solution can be separated into two phases by any one of the four techniques: (a) thermally induced gelation/crystalization; (b) non-solvent induced separation of solvent and polymer phases; (c) chemically induced phase separation, and (d) thermally induced spinodal decomposition. The polymer solution is separated in a controlled manner into either two distinct phases or two bicontinuous phases. Subsequent removal of the solvent phase usually leaves a porous structure of density less than the bulk polymer and pores in the micrometer ranges (ref. "Microcellular foams via phase separation" by A. T. Young, J. Vac. Sci. Technolol. A 4(3), May/June 1986). The steps involved in the preparation of these foams consists of choosing the right solvents for the polymers that needs to be lyophilized and preparing a homogeneous solution. Next, the polymer solution is subjected to a freezing and vacuum drying cycle. The freezing step phase separates the polymer solution and vacuum drying step removes the solvent by sublimation and/or drying leaving a porous polymer structure or an interconnected open cell porous foam.

Suitable solvents that should be generally suited as a starting place for selecting a solvent for the preferred absorbable aliphatic polyesters include but are not limited to solvents selected from a group consisting of formic acid, ethyl formate, acetic acid, hexafluoroisopropanol (HFIP), cyclic ethers (i.e. THF, DMF, and PDO), acetone, acetates of C2 to C5 alcohol (such as ethyl acetate and t-butylacetate), glyme (i.e. monoglyme, ethyl glyme, diglyme, ethyl diglyme, triglyme, butyl diglyme and tetraglyme) methylethyl ketone, dipropyleneglycol methyl ether, lactones (such as γ-valerolactone, δ-valerolactone, β-butyrolactone, γ-butyrolactone) 1,4-dioxane, 1,3-dioxolane, 1,3-dioxolane-2-one (ethylene carbonate), dimethlycarbonate, benzene, toluene, benzyl alcohol, p-xylene, naphthalene, tetrahydrofuran, N-methyl pyrrolidone, dimethylformamide, chloroform, 1,2-dichloromethane, morpholine, dimethylsulfoxide, hexafluoroacetone sesquihydrate (HFAS), anisole and mixtures thereof. Among these solvents, the preferred solvent is 1,4- dioxane. A homogeneous solution of the polymer in the solvent is prepared using standard techniques.

Accordingly, as will be appreciated, the applicable polymer concentration or amount of solvent, which may be utilized, will vary with each system. Suitable phase diagram curves for several systems have already been developed. However, if an appropriate curve is not available, this can be readily developed by known techniques. For example, a suitable technique is set forth in Smolders, van Aartsen and Steenbergen, Kolloid-Z. u. Z. Polymere, 243, 14 (1971). As a general guideline the amount of polymer in the solution can vary from about 0.5% to about 90% and preferably will vary from about 0.5% to about 30% by weight depending to a large extent on the solubility of the polymer in a given solvent and the final properties of the foam desired.

Additionally, solids may be added to the polymer-solvent system. The solids added to the polymer-solvent system preferably will not react with the polymer or the solvent. Suitable solids include materials that promote tissue regeneration or regrowth, buffers, reinforcing materials or porosity modifiers. Suitable solids include, but are not limited to, particles of demineralized bone, calcium phosphate particles, or calcium carbonate particles for bone repair, leachable solids for pore creation and particles of bioabsorbable polymers not soluble in the solvent system as reinforcing or to create pores as they are absorbed. Suitable leachable solids include but are not limited nontoxic leachable materials selected from the group consisting of salts (i.e. sodium chloride, potassium chloride, calcium chloride, sodium tartrate, sodium citrate, and the like) biocompatible mono and disaccharides (i.e. glucose, fructose, dextrose, maltose, lactose and sucrose), polysaccharides (i.e. starch, alginate), water soluble proteins (i.e. gelatin and agarose). Generally all of these materials will have an average diameter of less than about 1 mm and preferably will have an average diameter of from about 50 to about 500 $\mu$m. The particles will generally constitute from about 1 to about 50 volume percent of the total volume of the particle and polymer-solvent mixture (wherein the total volume percent equals 100 volume percent). The leachable materials can be removed by immersing the foam with the leachable material in a solvent in which the particle is soluble for a sufficient amount of time to allow leaching of substantially all of the particles, but which does not dissolve or detrimentally alter the foam. The preferred extraction solvent is water, most preferably distilled-deionized water. This process is described in U.S. Pat. No. 5,514,378 hereby incorporated herein by reference (see column 6). Preferably the foam will be dried after the leaching process is complete at low temperature and/or vacuum to minimize hydrolysis of the foam unless accelerated absorption of the foam is desired.

After the polymer solvent mixture is formed the mixture is then solidified. For a specific polymer-solvent system, the solidification point, the melt temperature and the apparent glass transition of the polymer-solvent system can be determined using standard differential scanning calorimetric (DSC) techniques. In theory, but in no way limiting the scope of the present invention, it is believed that as a polymer solvent system is cooled down an initial solidification occurs at about or below the freezing point of the solvent. This corresponds to the freezing of a substantial portion of the solvent in the system. The initial freezing appears as a first exothermic peak. A second freezing point occurs when the remaining solvent associated with the polymer solidifies. The second freezing point is marked by a second exothermic peak. The apparent Tg is the temperature at which the fully frozen system displays the first endothermic shift on reheating.

An important parameter to control is the rate of freezing of the polymer-solvent system. The type of pore morphology that gets locked in during the freezing step is a function of the solution thermodynamics, freezing rate, temperature to which it is cooled, concentration of the solution, homogeneous or heterogenous nucleation etc. Detailed description of these phase separation phenomenon can be found in the references provided herein ("Microcellular foams via phase separation" by A. T. Young, J. Vac. Sci. Technol. A 4(3), May/June 1986; and "Thermodynamics of Formation of Porous Poymeric Membrane from Solutions" by S. Matsuda, Polymer J. Vol. 23, No. 5, pp 435–444, 1991).

The polymer solution previously described can be solidified in a variety of manners such as placing or injecting the solution in a mold and cooling the mold in an appropriate bath or on a refrigerated shelf. Alternatively, the polymer solution can be atomized by an atomizer and sprayed onto a cold surface causing solidification of the spray layer by layer. The cold surface can be a medical device or part thereof or a film. The shape of the solidified spray will be similar to the shape of the surface it is sprayed onto. Alternatively, the mixture after solidification can be cut or formed to shape while frozen. Using these and other processes the foams can be made or molded in a variety of shapes and sizes (i.e. tubular shapes, branched tubular shapes, spherical shapes, hemispherical shapes, three-dimensional polygonal shapes, ellipsoidal shapes (i.e. kidney shaped), toroidal shapes, conical shapes, frusta conical shapes, pyramidal shapes, both as solid and hollow constructs and combination thereof).

Alternatively, another method to make shaped foamed parts is to use a cold finger (a metal part whose surface represents the inside of the part we want to fabricate). The cold finger is dipped into a mixture of polymer in an appropriate solvent and removed. This is much like dipping an ice cream pop into warm chocolate that freezes to a hard, cold skin, or dipping a form into a latex of rubber to form gloves or condoms. The thickness and morphology of the foam produced are a function of the temperature, dwell time and withdrawal rate of the cold finger in the mixture. Longer dwell, colder finger and slower withdrawal will produce a thicker coating. After withdrawal, the cold finger is placed on a fixture of large thermal mass that is in contact with the refrigerated tray of the lyophilizer. From this point the primary and secondary drying processes are as described above. This method is particularly well suited to making tubes, branched tubular structures or sleeves that may be shaped to fit devices or portions of an animal's anatomy (for repair, regeneration or augmentation of tissue).

Additionally, the polymer solution can be solidified with various inserts incorporated with the solution such as films, scrims, woven, nonwoven, knitted or braided textile structures. Additionally, the solution can be prepared in association with another structure such an orthopedic implant (e.g. screws, pins, nails, and plates) or vascular or branched tubular construct (as a scaffold for a vascularized or ducted organ). These inserts will be made of at least one biocompatible material and may be non-absorbable, absorbable or a combination thereof.

The polymer solution in a mold undergoes directional cooling through the wall of the mold that is in contact with the freeze dryer shelf, which is subjected to a thermal cycle. The mold and its surface can be made from virtually any material that does not interfere with the polymer-solvent system, though it is preferred to have a highly conducting material. The heat transfer front moves upwards from the lyophilizer shelf through the mold wall into the polymer solution. The instant the temperature of the mixture goes below the gellation and/or freezing point the mixture also phase separates.

The morphology of this phase separated system is locked in place during the freezing step of the lyophilization process and the creation of the open pores is initiated by the onset of vacuum drying resulting in the sublimation of the solvent. However, the mixture in container or mold that is cooled from a heat sink will solidify prior to completely freezing. Although the mixture may appear solid, initially there appears to be some residual solvent associated with the polymer that has not cystallized. It is theorized, but in no way limiting the present invention, that a freezing front moves through the mixture from the heat sink to complete the solidification after the mixture has apparently solidified. The material in front of the freezing front at a given time will not be as cold as the material behind the front and will not be in a completely frozen state.

We have discovered that if a vacuum is applied to the apparently solid polymer-solvent mixture immediately after it appears to solidify, a foam with a gradient structure having variable pore size and structure as well as channels can be created. Therefore, timing of the onset of the sublimation process (by pressure reduction i.e. vacuum drying) is a critical step in the process to create transitions in the structure. The timing of the onset of sublimation will be affected by the thickness of the foam being made, concentration of the solution, rate of heat transfer, and directionalities of the heat transfer. Those skilled in the art will appreciate that this process can be monitored and characterized for specific polymer-solvent systems by using thermocouples and monitoring the heat transfer rates of the foams at various depths and locations in the device being foamed. By controlling the sublimation process, structures with a gradient in pore morphology and anisotropy may be created. This process can lead to the creation of microstructures that mimic tissues such as cartilage, bone and skin. For example, channels will generally be formed if a vacuum is pulled immediately after the solution apparently solidifies. However, if the same solution is allowed to solidify further the foam will have larger pores closer to the surface where the vacuum is being drawn (opposite the heat sink) and smaller pores closer to the heat sink.

This process is the antitheses of the prior art process that focused on creating foams with a uniform microstructure (randomly interconnected pores), whereby the whole solution is completely frozen. And vacuum drying is applied only after a considerable amount of time is given for the completion of desired phase separation (U.S. Pat. Nos. 5,755,792 (Brekke); 5,133,755 (Brekke); 5,716,413 (Walter, et al.); 5,607,474 (Athanasiou, et al.); 5,686,091 (Leong, et al.); 5,677,355 (Shalaby, et al.); and European disclosures E0274898 (Hinsch) and EPA 594148 (Totakura)).

Figure 4:
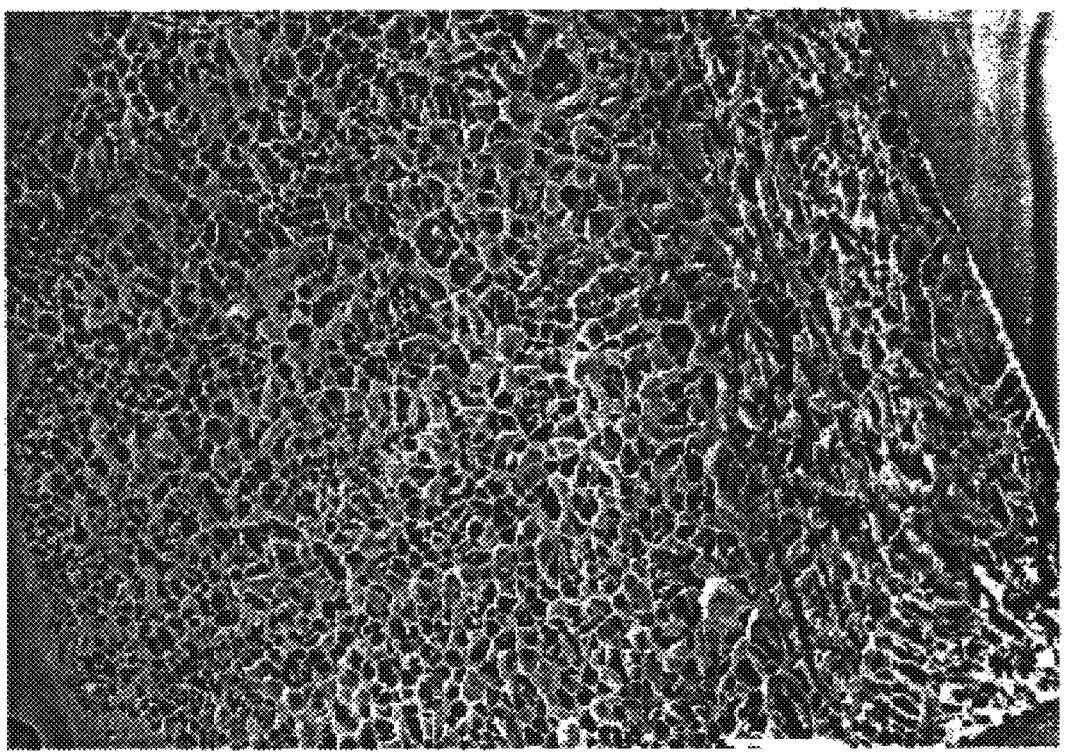
FIG. 4 is a scanning electron micrograph of the cross section of a gradient foam made from a 50/50 blend of 40/60 ε-caprolactone-co-(L)lactide copolymer and 35/65 ε-caprolactone-co-glycolide copolymer.

Foams with various structures are shown in FIGS. 2, 3, and 4. For example, as shown in FIG. 3 the orientation of the major axis of the pores may be changed from being in the same plane as the foam to being oriented perpendicular to the plane of the foam. By way of theory, but in no way limiting the scope of this invention, it is believed that this in conventional foam processing as the solvent crystallizes a freezing front moves through the solution solidifying the solution in crystalline layers parallel to the freezing front. However, if a vacuum is pulled before the solution completely freezes, the morphology of the foam results in pores being formed generally aligned parallel to the vacuum source. As is illustrated in FIG. 3.

As can be seen from FIG. 3 the pore size can be varied from a small pore size generally between about 10 µm and about 60 µm to a larger size of from about 60 µm to about 200 µm in a porous gradient foam. Again this results from pulling a vacuum on the apparently solidified solution before it is completely solidified. The polymer concentration in the solution and the cooling rates are also important parameters in controlling the cell size. Ideally the foam structure could be created to serve as a template to restore human tissue junctions such as the cartilage to bone junction present in joints. This foam would progress form a small round pores to larger column-like (i.e. with a diameter to length ratio of at least 2 to 1) pores. Additionally, the stiffness of the foam can controlled by the foams structure or blending two different polymers with different Young's moduli.

Foams can also have channels as is illustrated in FIG. 2. The channels formed by this process may traverse the thickness of the foam and generally range in diameter from about 30 to about 200 µm in diameter. The channels generally are at least two times the channel's average diameter and preferably are at least four times the channel's average diameter and most preferably at least eight times the channel's average diameter. The channel size and diameter of course will be selected based on the desired functionality of the channel such as cell invasion, nutrient diffusion or as a avenue for vascularization.

One skilled in the art can easily visualize that such a directionality can be created in any three dimensions by designing an appropriate mold and subjecting the walls of such a mold to different temperatures if needed. The following types of gradient structures can be made by variation in the pore size and/or shape through the thickness with a uniform composition: pores of one type and size for a certain thickness followed by another type and size of pores, etc; compositional gradient with predominantly one composition on one side and another one on the other with a transition from one entity to the other; a thick skin comprising low porosity of low pore size layer followed by a large pore size region; foams with vertical pores with a spatial organization these vertical pores can act as channels for nutrient diffusion the making of these in 3D molds to create 3D foams with the desired microstructure combinations of compositional and architectural gradient. Generally the foams formed in containers or molds will have a thickness in the range of from about 0.25 mm to about 100 mm and preferably will have a thickness of from about 0.5 mm to about 50 mm. Thicker foams can be made but the lyophilization cycle times may be quite long, the final foam structures may be more difficult to control and the residual solvent content may be higher.

As previously described the inventive process cycle for producing biocompatible foam is significantly reduced by performing the sublimation step above the apparent glass transition temperature and below the solidification temperature of the mixture (preferably just below the solidification temperature). The combined cycle time of (freezing+ primary drying+secondary drying) is much faster than is described in the prior art. For example, the combined cycle for aliphatic polyesters using volatile solvents is generally less than 72 hours, preferably less than 48 hours, more preferably less than 24 hours and most preferably less than 10 hours. In fact the combined cycle can be performed with some aliphatic polyesters in less than 3 hrs for foams of thickness 1 mm or less; less than 6 hrs for foams of thickness around 2 mm and less than 9 hrs for foams of thickness around 3 mm. Compare this with prior art which is typically 72 hours or greater. The residual solvent concentrations in these foams made by this process will be very low. As described for aliphatic polyesters foams made using 1,4-dioxane as a solvent the residual concentration of 1,4-dioxane was less than 10 ppm (parts per million) more preferably less than 1 ppm and most preferably less than 100 ppb (parts per billion).

One skilled in the art can easily visualize that such a directionality can be created in any three-dimensions by designing an appropriate mold and subjecting the walls of such a mold to different temperatures if needed. The following types of gradient structures can be made by this invention
1. variation in the pore size and/or shape through the thickness with a uniform composition,
2. pores of one type and size for a certain thickness followed by another type and size of pores, etc
3. compositional gradient with predominantly one composition on one side and another composition on the other with a transition from one entity to the other
4. a thick skin comprising low porosity of low pore size layer followed by a large pore size region
5. foams with vertical pores with a spatial organization. . . these vertical pores can act as channels for nutrient diffusion
6. the making of these in three-dimensional molds to create three-dimensional foams with the desired microstructure.
7. combinations of compositional and architectural gradient Additionally, various proteins (including short chain peptides), growth agents, chemotatic agents and therapeutic agents (antibiotics, analgesics, anti-inflammatories, anti-rejection (e.g. immunosuppressants) and anticancer drugs), or ceramic particles can be added to the foams during processing, adsorbed onto the surface or back filled into the foams after the foams are made. For example, the pores of the foam may be partially or completely filled with biocompatible resorbable synthetic polymers or biopolymers (such as collagen or elastin) or biocompatible ceramic materials (such as hydroxyapatite) and combinations thereof (that may or may not contain materials that promote tissue growth through the device). Suitable materials include but are not limited to autograft, allograft, or xenograft bone, bone marrow, morphogenic proteins (BMP's), epidermal growth factor (EGF), fibroblast growth factor (FgF), platelet derived growth factor (PDGF), insulin derived growth factor (IGF-I and IGF-II), transforming growth factors (TGF-β), vascular endothelial growth factor (VEGF) or other osteoinductive or osteoconductive materials known in the art. Biopolymers could also be used as conductive or chemotactic materials, or as delivery vehicles for growth factors. Examples could be recombinant or animal derived collagen or elastin or hyaluronic acid. Bioactive coatings or surface treatments could also be attached to the surface of the materials. For example, bioactive peptide sequences (RGD's) could be attached to facilitate protein adsorption and subsequent cell tissue attachment. Therapeutic agents may also be delivered with these foams.

In another embodiment of the present invention, the polymers and blends that are used to form the foam can contain therapeutic agents. To form these foams, the previously described polymer would be mixed with a therapeutic agent prior to forming the foam or loaded into the foam after it is formed. The variety of different therapeutic agents that can be used in conjunction with the foams of the present invention is vast. In general, therapeutic agents which may be administered via the pharmaceutical compositions of the invention include, without limitation: anti-infectives such as antibiotics and antiviral agents; chemotherapeutic agents (i.e. anticancer agents); anti-rejection agents; analgesics and analgesic combinations; anti-inflammatory agents; hormones such as steroids; growth factors (bone morphogenic proteins (i.e. BMP's 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-β I-III), vascular endothelial growth factor (VEGF)); and other naturally derived or genetically engineered proteins, polysaccharides, glycoproteins, or lipoproteins. These growth factors are described in *The Cellular and Molecular Basis of Bone Formation and Repair* by Vicki Rosen and R. Scott Thies, published by R. G. Landes Company hereby incorporated herein by reference.

Foams containing bio-active materials may be formulated by mixing one or more therapeutic agents with the polymer used to make the foam or with the solvent or with the polymer-solvent mixture and foamed. Alternatively, a therapeutic agent could be coated on to the foam preferably with a pharmaceutically acceptable carrier.

Any pharmaceutical carrier can be used that does not dissolve the foam. The therapeutic agents, may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001 percent to about 70 percent, more typically about 0.001 percent to about 50 percent, most typically about 0.001 percent to about 20 percent by weight of the matrix. The quantity and type of polymer incorporated into the drug delivery matrix will vary depending on the release profile desired and the amount of drug employed.

Upon contact with body fluids the drug will be released. If the drug is incorporated into the foam then as the foam undergoes gradual degradation (mainly through hydrolysis) the drug will be released. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like. Following this or similar procedures, those skilled in the art will be able to prepare a variety of formulations.

The foam may also serve as a scaffold for the engineering of tissue. The porous gradient structure would be conducive to growth of cells. As outlined in previous patents (Vacanti, U.S. Pat. No. 5,770,417), cells can be harvested from a patient (before or during surgery to repair the tissue) and the cells can be processed under sterile conditions to provide a specific cell type (i.e., pluripotent cells, stem cells or precursor cells such as the mesenchymal stem cells described in Caplan, U.S. Pat. No. 5,486,359, etc.). Suitable cell that may be contacted or seeded into the foam scaffolds include but are not limited to myocytes, adipocytes, fibromyoblasts, ectodermal cell, muscle cells, osteoblast (i.e. bone cells), chondrocyte (i.e. cartilage cells), endothelial cells, fibroblast, pancreatic cells, hepatocyte, bile duct cells, bone marrow cells, neural cells, genitourinary cells (including nephritic cells) and combinations thereof. Various cellular strategies could be used with these scaffolds (i.e., autogenous, allogenic, xenogeneic cells etc.). The cells could also contain inserted DNA encoding a protein that could stimulate the attachment, proliferation or differentiation of tissue. The foam would be placed in cell culture and the cells seeded onto or into the structure. The foam would be maintained in a sterile environment and then implanted into the donor patient once the cells have invaded the microstructure of the device. The in vitro seeding of cells could provide for a more rapid development and differentiation process for the tissue. It is clear that cellular differentiation and the creation of tissue specific extracellular matrix is critical for the tissue engineering of a functional implant.

The option for seeding different cell types into the different pore structures would be available to investigators. Schaufer et al., have demonstrated that different cell types (i.e. stromal cells and chondrocytes) can be cultured on different structures. The structures can be combined after a short period of time and the entire structure can be placed back in cell culture so a biphasic tissue structure can be generated for implantation. A gradient structure would also allow for co-cultured tissue scaffolds to be generated. (Schaefer, D. et al.). Additionally, radio-opaque markers may be added to the foams to allow imaging after implantation. After a defined period of in vitro development (for example 3 weeks), the tissue engineered implant would be harvested and implanted into the patient. If an acellular strategy is pursued, then the sterile acellular scaffolds would be used to replace damaged or traumatized tissue.

The foam scaffolds of the present invention may be sterilized using conventional sterilization process such as radiation based sterilization (i.e. gamma-ray), chemical based sterilization (ethylene oxide) or other appropriate procedures. Preferably the sterilization process will be with ethylene oxide at a temperature between 52–55° C. for a time of 8 hours or less. After sterilization the foam scaffolds may be packaged in an appropriate sterilize moisture resistant package for shipment and use in hospitals and other health care facilities.

In another embodiment of the present invention the foam may have a fibrous fabric fused to the top or bottom surface. This way, surface properties of the structure can be controlled such as porosity, permeability, degradation rate and mechanical properties. The fibrous fabric can be produced via an electrostatic spinning process in which a fibrous layer can be built up on a lyophilized foam surface. The electrostatic spinning process is a method that has been used to make fibers. Electrostatic spinning of many polymeric materials has been described in the following patents and articles: U.S. Pat. No. 4,522,709; U.S. Pat. No. 5,024,789; U.S. Pat. No. 5,311,884; U.S. Pat. No. 5,522,879; "Nanometre diameter fibers of polymer, produced by electrospinning," *Nanotechnology* 1 (1996) 216–233; "Structure and morphology of small diameter electrospun aramid fibres," *Polymer Inter.*, 36 (1995) 195–201, "Carbon nanofiber from polyacrylonitrile and mesophase pitch," *Journal of Advanced Materials*, Vol. 3, No. 1, (1999) 36–41 which are hereby incorporated herein by reference. This process may also be used with the aliphatic polyesters previously described in this application using appropriate solvents. The solvents used in the foaming process may also be used for electrostatic spinning.

Figure 12:
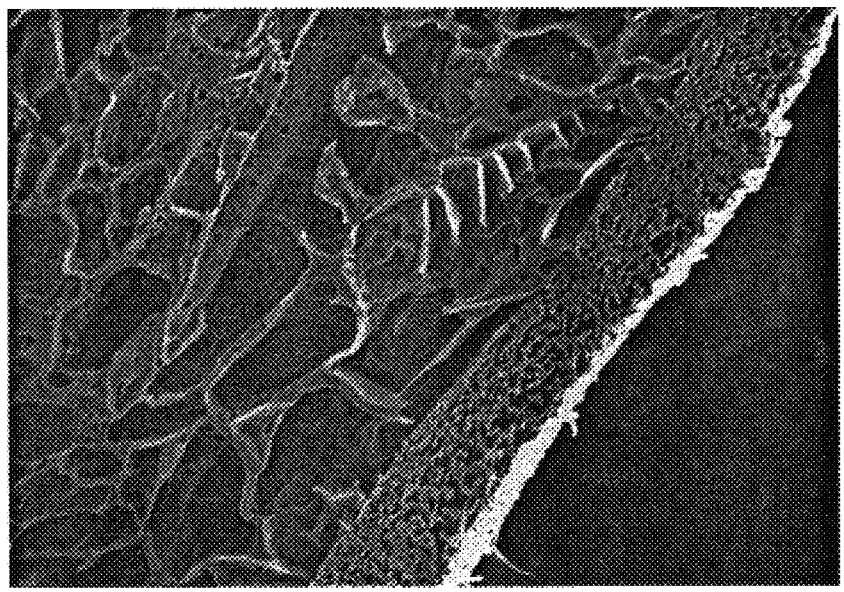
FIG. 12 is a photomicrograph of a cross-section of an electrostatically spun fibrous layer fused to a foam substrate (both materials are 60/40 copolymers of (L) lactide and ε-caprolactone).
Figure 13:
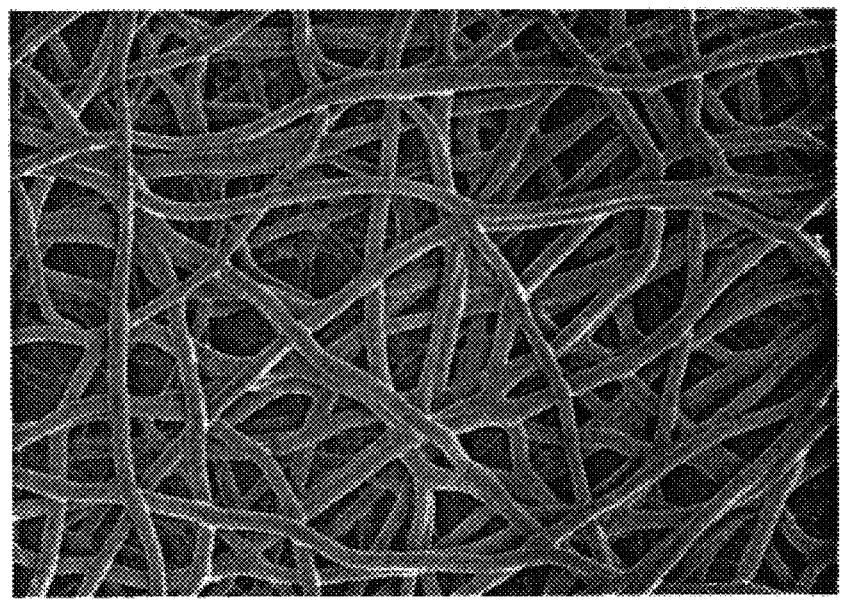
FIG. 13 is a photomicrograph of the surface porosity of the electrostatically spun layer shown in FIG. 12.

In this process, an electrical force is applied to the polymeric solution that overcomes the surface tension of the solution, forming a charged jet. This jet of solution is ejected, dried and solidified onto a grounded substrate. By controlling the spinning conditions, the resulting fibers can range from about 0.1 $\mu$m to about 20 $\mu$m and preferably will range from about 0.3 $\mu$m to about 5.0 $\mu$m. The substrate surface in this case would be a lyophilized foam. Two examples of such a construct, with a fibrous layer on top of a foam layer, are shown in FIGS. 12 and 13. These layered structures may be made of at least one biocompatible material and may be non-absorbable, absorbable or a combination thereof.

The composition, thickness and porosity of the fibrous layer may be controlled to provide the desired mechanical and biological characteristics. For example the bioabsorption rate of the fibrous layer may be selected to provide a longer or shorter bioabsorption profile as compared to the underlying foam layer. Additionally, fibrous layer may provide greater structural integrity to the composite so that mechanical force may be applied to the fibrous side of the structure. For example the fibrous layer could allow the use of sutures, staples or various fixation devices to hold the composite in place. As a general guideline but in no way limiting the scope of the invention it is currently preferred that the fibrous layer comprise a layer of from about 1 micron to about 1000 microns in thickness.

One possible application of a foam structure with a fibrous surface layer is as a vascular graft. The layers in such a structure would form concentric cylinders, and the fibrous layer would provide a decreased permeability. The lyophilized foam structure could be optimized for cell infiltration either on the adventitial surface by smooth muscle cells or fibroblasts, or on the luminal surface by endothelial cells. The fibrous fabric layer would serve as a barrier to blood leakage, and would enhance the mechanical properties of the structure. Additionally, the fibrous layer would serve as a barrier to multiplying smooth muscle cells and would assist in the prevention of intimal hyperplasia.

Another possible application of such a hybrid foam/fabric structure is as a scaffold for breast regeneration. The fibrous layer would provide increased mechanical integrity, and would maintain the original shape of the scaffold. When a biopsy is taken or when a tumor is removed, the cavity could be filled with such a fibrous coated foam scaffold, which may or may not be injected with cells or bioactive agents.

Another possible application of such a foam/fabric structure is as a scaffold for meniscal tissue engineering. In this case, a wedge shaped implant could be made consisting of a fibrous coating encapsulating a lyophilized foam center. The cells could be injected into the center of the implant through the fibrous layer. This fabric surface layer would allow the diffusion of nutrients and waste products while limiting the migration of the cells out of the scaffold.

The following examples are illustrative of the principles and practice of this invention, although not limited thereto. Numerous additional embodiments within the scope and spirit of the invention will become apparent to those skilled in the art.

EXAMPLES

In the examples which follow, the polymers and monomers were characterized for chemical composition and purity (NMR, FT-IR), thermal analysis (DSC), molecular weight (inherent viscosity), and baseline and in vitro mechanical properties (Instron stress/strain).

$^1$H NMR was performed on a 300 MHz NMR using $CDCl_3$ or HFAD (hexafluoroacetone sesqua deutrium oxide) as a solvent. Thermal analysis of segmented polymers and monomers was performed on a Dupont 912 Differential Scanning Calorimeter (DSC). Inherent viscosities (I.V., dL/g) of the polymers and copolymers were measured using a 50 bore Cannon-Ubbelhode dilution viscometer immersed in a thermostatically controlled water bath at 25° C. utilizing chloroform or hexafluoroisopropanol (HFIP) as the solvent at a concentration of 0.1 g/dL.

In these examples certain abbreviations are used such as PCL to indicate polymerized ε-caprolactone, PGA to indicate polymerized glycolide, PLA to indicate polymerized (L)lactide. Additionally, the percentages in front of the copolymer indicates the respective mole percentages of each constituent.

Example 1
Preparation of a Foam with Random Microstructure (no preferred architecture)

Step A. Preparing 5% wt./wt. homogeneous solution of 35/65 PCL/PGA in 1,4-Dioxane A 5% wt./wt. polymer solution is prepared by dissolving 1 part of 35/65 PCL/PGA with 19 parts of the solvent—1, 4-dioxane. The 35/65 PCL/PGA copolymer was made substantially as described in Example 8. The solution is prepared in a flask with a magnetic stir bar. For the copolymer to dissolve completely, it is recommended that the mixture is gently heated to 60±5° C. and continuously stirred for a minimum of 4 hours but not exceeding 8 hours. A clear homogeneous solution is then obtained by filtering the solution through an extra coarse porosity filter (Pyrex brand extraction thimble with fritted disc) using dry nitrogen to help in the filtration of this viscous solution.

Step B. Lyophilization

A laboratory scale lyophilizer—Freezemobile 6 of VIRTIS was used in this experiment. The freeze dryer is powered up and the shelf chamber is maintained at 20° C. under dry nitrogen for approximately 30 minutes. Thermocouples to monitor the shelf temperature are attached for monitoring. Carefully fill the homogeneous polymer solution prepared in Step A. into the molds just before the actual start of the cycle. A glass mold was used in this example but a mold made of any material that is inert to 1,4-dioxane; has good heat transfer characteristics; and has a surface that enables the easy removal of the foam can be used. The glass mold or dish used in this example weighed 620 grams, was optical glass 5.5 mm thick, and cylindrical with a 21 cm outer diameter and a 19.5 cm inner diameter. The lip height of the dish was 2.5 cm. Next the following steps are followed in a sequence to make a 2 mm thick foam:

(i). The glass dish with the solution is carefully placed (without tilting) on the shelf of the lyophilizer, which is maintained at 20° C. The cycle is started and the shelf temperature is held at 20° C. for 30 minutes for thermal conditioning.

(ii). The solution is then cooled to −5° C. by cooling the shelf to −5° C.

(iii). After 60 minutes of freezing at −5° C., a vacuum is applied to initiate primary drying of the dioxane by sublimation. One hour of primary drying under vacuum at −5° C. is needed to remove most of the solvent. At the end of this drying stage typically the vacuum level reached about 50 mTorr or less.

(iv). Next, secondary drying under a 50 mTorr vacuum or less was done in two stages to remove the adsorbed dioxane. In the first stage, the shelf temperature was raised to 5° C. and held at that temperature for 1 hour. At the end of the first stage the second stage of drying was begun. In the second stage of drying, the shelf temperature was raised to 20° C. and held at that temperature for 1 hour.

(v). At the end of the second stage, the lyophilizer is brought to room temperature and the vacuum is broken with nitrogen. The chamber is purged with dry nitrogen for approximately 30 minutes before opening the door.

The steps described above are suitable for making foams that are about 2 mm thick or less. As one skilled in the art would know, the conditions described herein are typical and operating ranges depend on several factors e.g.: concentration of the solution; polymer molecular weights and compositions; volume of the solution; mold parameters; machine variables like cooling rate, heating rates; and the like. FIG. 1 shows a SEM of a cross section of the foam produced following the process set forth in this example. Note the random microstructure (not a preferred architecture) of this foam.

Example 2
Preparation of a Foam with Vertical Channels

This example describes the making of a 35/65 PCL/PGA foam with vertical channels that would provide pathways for nutrient transport and guided tissue regeneration.

We used a FTS Dura Dry Freeze dryer with computer control and data monitoring system to make this foam. First step in the preparation of this foam was to generate a homogeneous solution. A 10% wt./wt. homogeneous solution of 35/65 PCL/PGA was made in a manner similar to that described in Example 1, Step A. The polymer solution was carefully filled into a dish just before the actual start of the cycle. The dish weighed 620 grams, was optical glass 5.5 mm thick, and cylindrical with a 21 cm outer diameter and a 19.5 cm inner diameter. The lip height of the dish was 2.5 cm. Next the following steps are followed in sequence to make a 2 mm thick foam with the desired architecture:

(i). The solution filled dish was placed on the freeze dryer shelf that was precooled to −17° C. The cycle was started and the shelf temperature was held at −17° C. for 15 minutes quenching the polymer solution.

(ii). After 15 minutes of quenching to −17° C., a vacuum was applied to initiate primary drying of the dioxane by sublimation and held at 100 milliTorr for one hour.

(iii). Next, secondary drying was done at 5° C. for one hour and at 20° C. for one hour. At each temperature the vacuum level was maintained at 20 mTorr.

(iv). At the end of the second stage, the lyophilizer was brought to room temperature and the vacuum was broken with nitrogen. The chamber was purged with dry nitrogen for approximately 30 minutes before opening the door.

FIG. 2 is a SEM picture that shows a cross section of the foam with vertical channels. These channels run through the thickness of the foam.

Example 3
Architecturally Gradient Foam

This example describes the making of a foam that has a gradient in foam morphology as shown in FIG. 3 using a 10% solution of 35/65 ε-caprolactone-co-glycolide. The method used to make such a foam is similar to the description given in Example 2 with one difference. In step (ii) of the lyophilization process the time for which the solution is kept at the freezing step is 30 minutes.

FIG. 3 is a scanning electron micrograph of a cross section of this foam. Note the variation in the pore size and pore shape through the thickness of the foam.

Example 4
Transcompositional Foam

This example describes the making of a foam that has a compositional gradient and not necessarily a morphological gradient. Such a foam is made from polymer solutions that have been made from physical mixtures of two or more polymers. This example describes a transcompositional foam made from 35/65 PCL/PGA and 40/60 PCL/PLA Step A. Preparing a solution mixture of 35/65 PCL/PGA and 40/60 PCL/PLA in 1,4-Dioxane In the preferred method the two separate solutions are first prepared (a) a 10% wt/wt polymer solution of 35/65 PCL/PGA and (b) a 10% wt/wt 40/60 PCL/PLA. Once these solutions are prepared as described in Example 1, equal parts of each solution was poured into one mixing flask. The polymers used to make these solutions are described in Examples 8 and 9. A homogeneous solution of this physical mixture was obtained by gently heating to 60±5° C. and continuously stirring using a magnetic stir bar for approximately 2 hours.

Step B. Lyophilization cycle

We used an FTS Dura Dry Freeze dryer with computer control and data monitoring system to make this foam. The first step in the preparation of such a foam was to generate a homogeneous solution as described in Step A. The solution was carefully filled into a dish just before the actual start of the cycle. The cylindrical glass dish weighed 117 grams, was optical glass 2.5 mm thick and cylindrical with a 100 mm outer diameter and a 95 mm inner diameter. The lip height of the dish was 50 mm. Next the following steps were followed in sequence to make a 25 mm thick foam with the transcompositional gradient:

(i). The solution filled dish was placed on the freeze dryer shelf and the solution conditioned at 20° C. for 30 minutes. The cycle was started and the shelf temperature was set to −5° C. with a programmed cooling rate of 0.5° C./min.

(ii). The solution was held at the freezing condition (−5° C.) for 5 hours.

(iii). Vacuum was applied to initiate primary drying of the dioxane by sublimation and held at 100 milliTorr for 5 hours.

(iv). Next, secondary drying was done at 5° C. for 5 hours and at 20° C. for 10 hours. At each temperature the vacuum level was maintained at 20 mTorr.

(v). At the end of the second stage, the lyophilizer was brought to room temperature and the vacuum was broken with nitrogen. The chamber was purged with dry nitrogen for approximately 30 minutes before opening the door.

Figure 5:
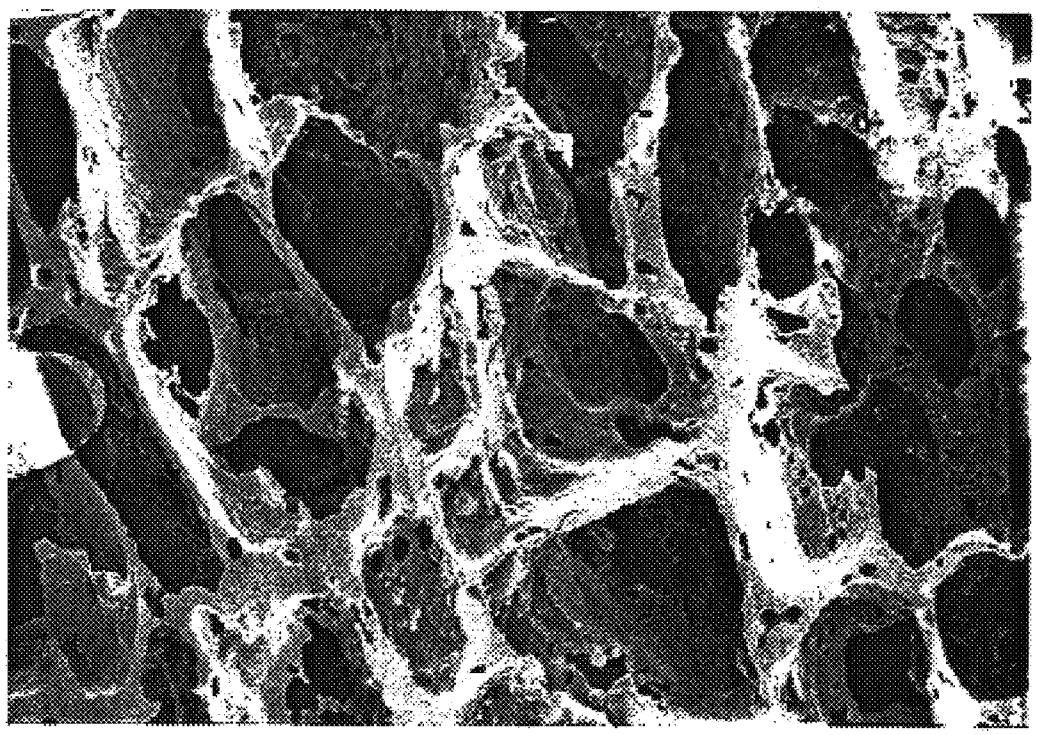
FIG. 5 is a scanning electron micrograph of a cross section of the top portion of a gradient foam made from a 50/50 blend of 40/60 ε-caprolactone-co-(L)lactide copolymer and 35/65 ε-caprolactone-co-glycolide copolymer.
Figure 6:
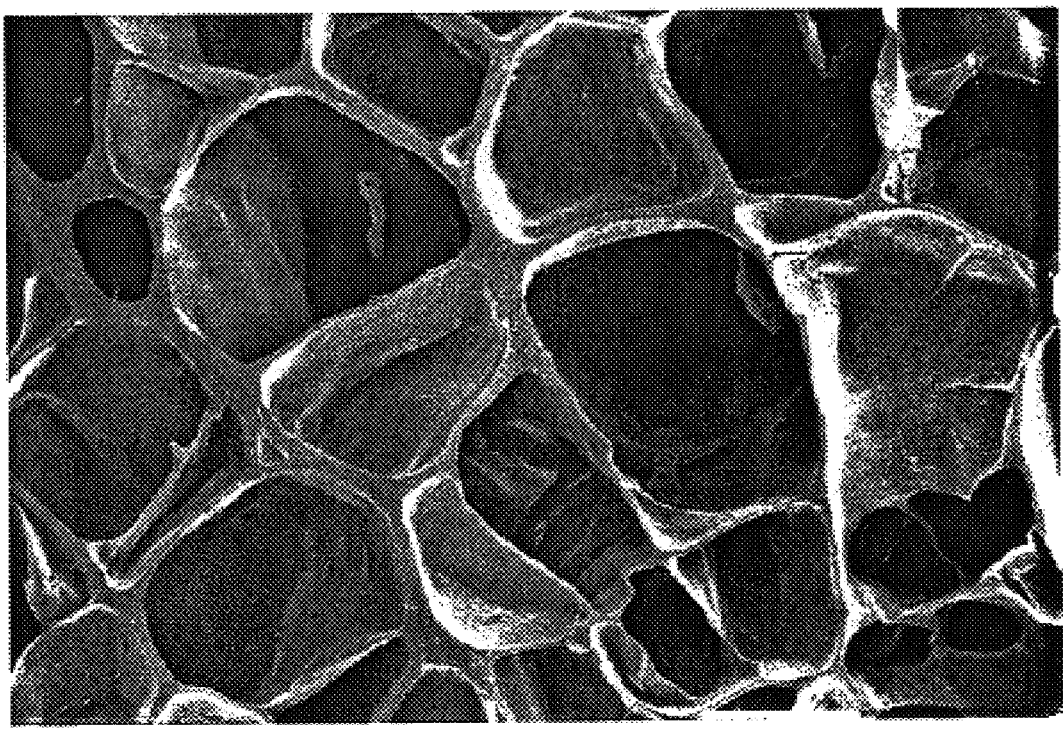
FIG. 6 is a scanning electron micrograph of a cross section of the bottom portion of a gradient foam made from a 50/50 blend of 40/60 ε-caprolactone-co-(L)lactide copolymer and 35/65 ε-caprolactone-co-glycolide copolymer.

The foam has a gradient in chemical composition which is evident from a close scrutiny of the foam wall morphology as shown in FIGS. 4, 5 and 6. The gradient in the chemical composition was further supported by NMR data as detailed below:

Foam sample produced by the above method and which was approximately 25 mm thick was characterized for mole % composition. The foam sample is composed of a physical blend of PCL/PLA and PCL/PGA. Slices of the foam sample were prepared and analyzed to confirm that the material was a compositional gradient. The sample slices were identified as 1) foam IA (top slice), 2) foam IB (top middle slice), 3) foam IC (bottom middle slice), 4) foam ID (bottom slice). The NMR sample preparation consisted of dissolving a 5 mg of material into 300 μL hexafluoroacetone sesqua deutrium oxide (HFAD) and then diluting with 300 μL of $C_6D_6$.

| 1H NMR Results: Mole % Composition | | | |
|---|---|---|---|
| Sample ID | PLA | PGA | PCL |
| Foam IA | 47.2 | 12.4 | 40.5 |
| Foam IB | 12.3 | 51.3 | 36.5 |
| Foam IC | 7.7 | 56.5 | 35.8 |
| Foam ID | 7.8 | 56.3 | 35.8 |

The NMR results indicate that the foam samples have a gradient with respect to composition. The top layer of the foam is high in PLA concentration (47 mole %), whereas the bottom layer of the foam is high in PGA concentration (56 mole %). These results suggest that the PCL/PGA copolymer and the PCL/PLA copolymer have differences in their phase separation behaviors during the freezing step and formed a unique compositionally gradient foam.

Example 5
Transstructural Foam

This example describes the making of a foam that has a compositional and structural gradient and not necessarily a morphological gradient. Such a foam is made from polymer solutions that have been made by physical mixtures of two or more polymers. This example describes a transcompositional foam made from 35/65 PCL/PLA (as described in Example 9) and 95/5 PLA/PCL (a random copolymer with an IV of 1.8 in HFIP measured as described herein). Note, 35/65 PCL/PLA is a soft elastomeric copolymer while 95/5 PLA/PCL is a relatively stiff copolymer. The combination of the two provides a compositional as well as structural gradient. This foam is made using the steps outlined in Example 4 starting from a homogeneous 50/50 physical mixture of a 10% wt./wt. solution of 35/65 PCL/PLA and 10% wt./wt. Solution of 95/5 PLA/PCL in 1,4 dioxane. Such a transcompositional foam will provide a good template for tissue junctions such as bone-cartilage interfaces.

Example 6
Cell Culture and Differentiation Data

Films made from 95/5 PLA/PGA, 90/10 PGA/PLA, 95/5 PLA/PCL, 75/25 PGA/PCL and 40/60 PCL/PLA were tested. Tissue culture polystyrene (TCPS) was used as a positive control for all the assays. Before testing, polymer discs were positioned at the bottom of a 24-well ultralow cluster dish and were pre-wetted in growth media for 20 min.

The 95/5 PLA/PGA copolymer used in this example was a random copolymer with an IV of 1.76 as determined in HFIP at 25° C., which is currently used in Panacryl™ suture (Ethicon Inc., Somerville, N.J.). The 90/10 PGA/PLA copolymer was a random copolymer with an IV of 1.74 as determined in HFIP at 25° C., which is currently used in Vicyl™ suture (Ethicon Inc., Somerville, N.J.). The 95/5 PLA/PCL polymer was made as described in Example 10, with an IV of 2.1 as determined in HFIP at 25° C. The 75/25 PG/PCL copolymer is a segmented block copolymer with an IV of 1.85 and is described in U.S. Pat. No. 5,133,739 this copolymer is currently used in Monocryl™ sutures (Ethicon Inc., Somerville, N.J.). The 40/60 PCL/PLA copolymer used in this Example was made as described in Example 9 and had an IV of 1.44.

Cell attachment and proliferation: Cells were seeded at 40,000/well in 24-well ultralow cluster dishes (Corning) containing the polymers. The ultralow cluster dishes are coated with a layer of hydrogel polymer, which retards protein and cell adhesion to the wells. Cell attachment to the biopolymers was determined following 24 hrs of incubation (N=3 for each polymer). The attached cells were released by trypsinization and the number of cells was determined using a heamacytometer. Cell proliferation was assessed by determining cell counts at days 3 and 6 following seeding.

Differentiation assays:

Alkaline phosphatase activity: Alkaline phosphatase activity was determined by a calorimetric assay using p-nitrophenol phosphate substrate (Sigma 104) and following manufacturers instruction. Briefly, cells were seeded on the films or meshes at a density of 40,000 cells/well and incubated for 1, 6, 14, and 21 d. Once cells reached confluence at day 6 they were fed with mineralization medium (growth medium supplemented with 10 mM β-glycerophosphate, 50 µg/ml ascorbic acid). Alkaline phosphatase activity was determined in cell homogenates (0.05% Triton X-100) at the above time points. The quantity of protein in cell extracts was determined by micro BCA reagent from Pierce. Primary rat osteoblasts cultured on films and meshes were also stained for membrane-bound alkaline phosphatase using a histochemical staining kit (Sigma). For all the films and meshes three samples per group were tested.

Osteocalcin ELISA: Osteocalcin secreted into the medium by osteoblasts cultured on various films was quantified by ELISA (Osteocalcin ELISA kit, Biomedical Technologies Inc, Boston). Aliquots of media from the wells containing the polymer films were lyophilized prior to measurements of this protein by ELISA. Three samples for each polymer were tested and the ELISA was repeated twice.

Von Kossa staining

Three samples for each polymer were stained for mineralized tissue using Von Kossa silver nitrate staining.

Expression of alkaline phosphatase and osteocalcin mRNAs

The expression of alkaline phosphatase and osteocalcin mRNAs in cells was assessed by semi-quantitative reverse transcriptase polymerase chain reaction (RT-PCR) using RNA extracted from cells cultured for 21 d on the films. Seven days after seeding, the culture media was replaced with mineralization media (3 mM β-glycerophosphate and 50 µg/ml of ascorbic acid were added). The cells were cultured for additional 2 weeks, for a total period of 3 weeks. Total RNA was extracted from four samples per group using a RNeasy mini kit provided by Qiagen. The quality and amount of total RNA was measured for each polymer group. Total RNA was reverse transcribed to obtain cDNA using a reverse transcriptase reaction (Superscript II, Gibco). The cDNAs for osteocalcin, alkaline phosphatase, and Glyceraldehyde-3-phosphate-dehydrogenase (GAPDH) were amplified using a PCR protocol described previously (GIBCO BRL manufacturers instruction). The primer sequences (Table I) for osteocalcin, alkaline phosphatase, and GAPDH were obtained using the FASTA program (Genetic Computer Group, Madison, Wis.). Preliminary studies were also conducted to optimize the number of PCR cycles for each primer (Table II), and to determine the range of RNA, which exhibits proportionality to cDNA. The PCR products were electrophoreses on 1% (wt) agarose gels containing ethidium bromide. The gels were photographed under UV light and were evaluated by densitometry for the expression of osteocalcin and alkaline phosphatase mRNAs relative to GAPDH.

Statistical Analysis

Analysis of variance (ANOVA) with Tukey post hoc comparisons was used to assess levels of significance for all the assays.

TABLE I

Primers used in RT-PCR

| Gene | Species | Forward primer | Reverse primer | Size (bp) |
|---|---|---|---|---|
| Alkaline phosphatase | Rat | 5' ATCGCCTATCAGCTAAT GCAC | 5' GCAAGAAGAAGCCTTT GGG | 379 |
| Osteocalcin | Rat/ Human | 5'CAACCCCAATTGTGA CGAGC | 5'TGGTGCGATCCATCAC AGAG | 339 |
| GAPDH | Mouse/ Human/ Rat | 5'ACCACAGTCCATGCC ATCAC | 5'TCCACCACCCTGTT GCTGTA | 452 |

TABLE II

PCR optimization cycles

| Gene | cDNA (µl) | Cycles |
|---|---|---|
| Alkaline phosphatase | 1 | 25 |
| Osteocalcin | 1 | 35 |
| GAPDH | 1 | 23 |

Results

Figure 7A:
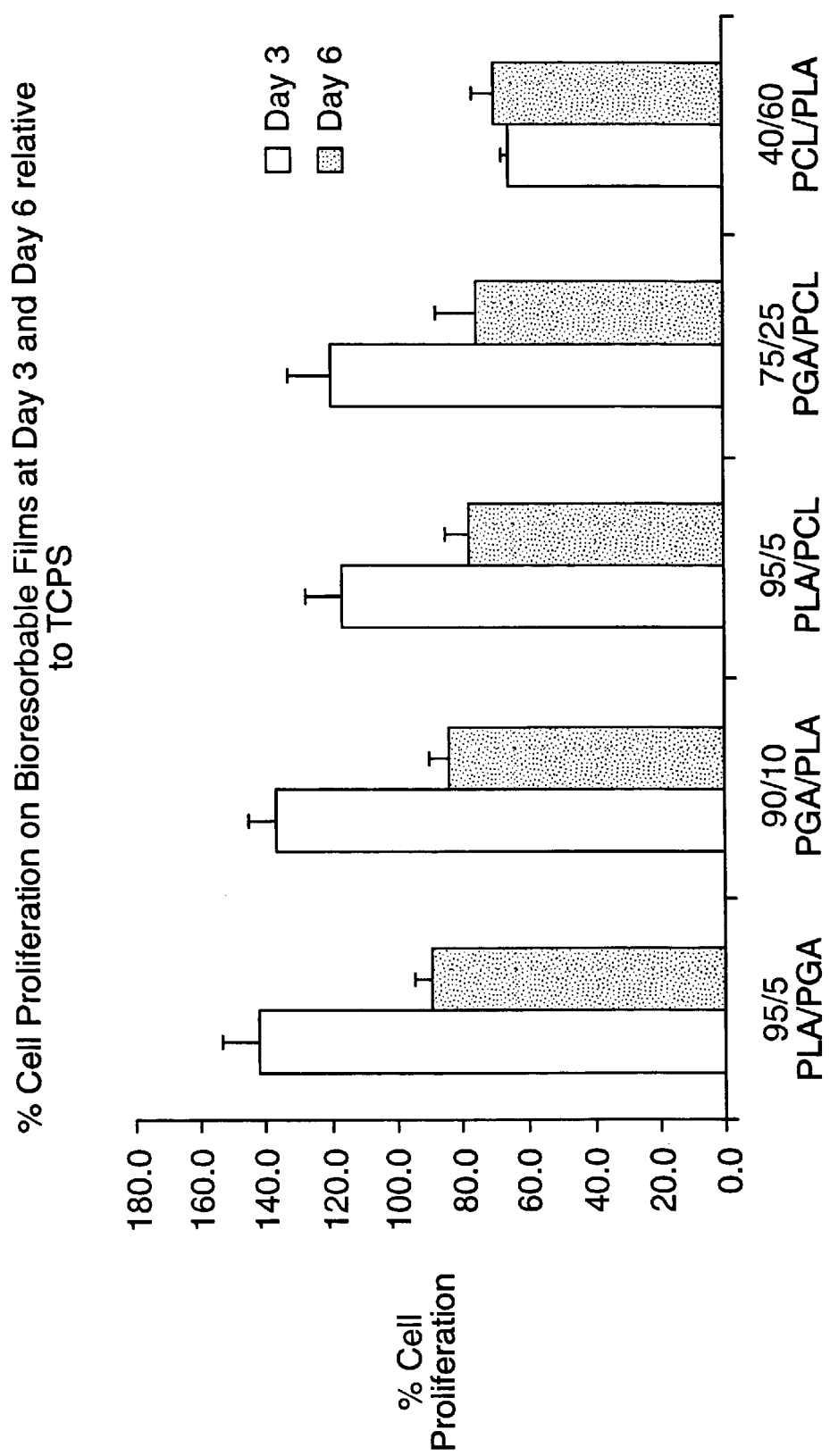
FIG. 7 is a graphical presentation of cell culture data, 7A, 7B and 7C.

Cell attachment and proliferation on bioresorbable polymers: No observable difference in cell morphology was evident between the various polymer films and as compared to TCPS. Cell attachment to the various biopolymer films was equivalent to TCPS following 24 h of incubation. At day 3, cells proliferated well on all films with the exception of 40/60 PCL/PLA, where proliferation was 60% relative to TCPS. Furthermore, 95/5 PLA/PGA and 90/10 PGA/PLA films supported a significantly (p<0.05) higher degree of cell proliferation compared to TCPS and 40/60 PCL/PLA (FIG. 7A).

Differentiation assay:

Alkaline phosphatase enzyme activity: The profile for alkaline phosphatase activity expressed by osteoblasts cultured on 95/5 PLA/PGA, 90/10 PGA/PLA and 95/5 PLA/ PCL films was similar to the profile observed on TCPS. Alkaline phosphatase specific activities were significantly (p<0.05) elevated for osteoblasts cultured on 40/60 PCL/PLA and 75/25 PGA/PCL films at days 14 and 21, respectively, compared to other films and TCPS (FIG. 7B)

Figure 7C:
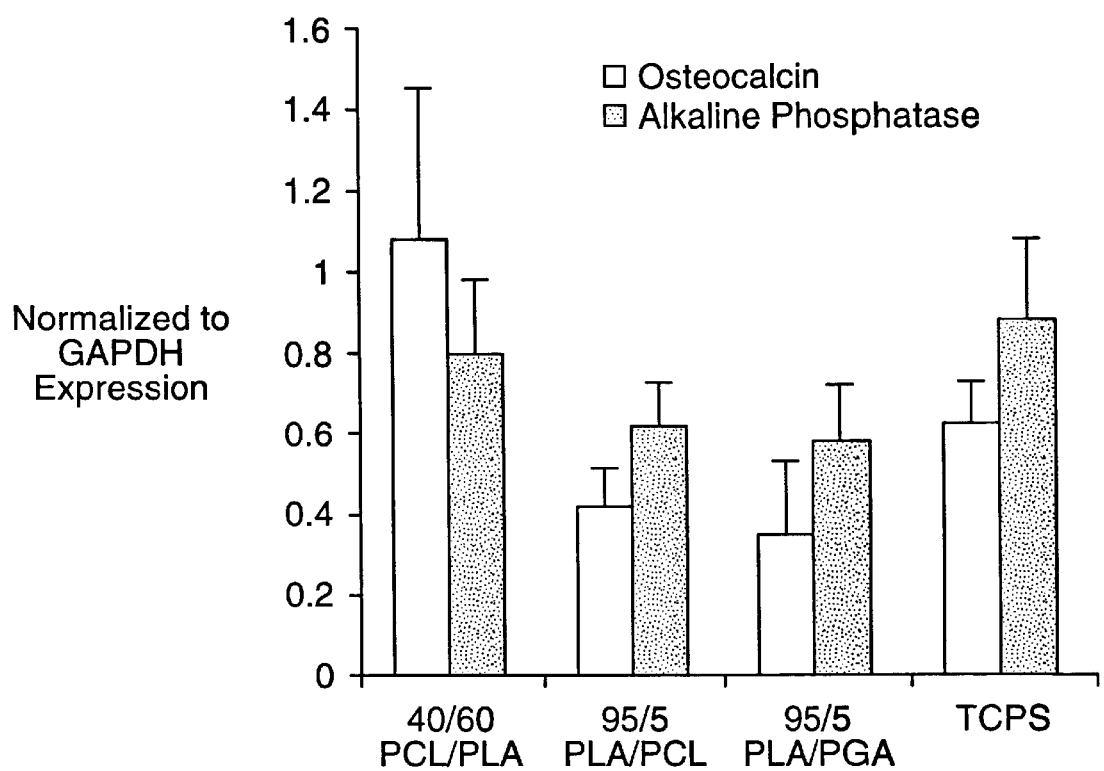

Expression of alkaline phosphatase and osteocalcin MRNA:

The expression of mRNAs for alkaline phosphatase, osteocalcin, and GAPDH for osteoblasts cultured on the 95/5 PLA/PGA, 40/60 PLA/PCL, 95/5 PLA/PCL films, and TCPS were evaluated by densitometry. The results are depicted in FIG. 7C. It should be noted that the data in FIG. 7B is at best semi-quantitative. Nevertheless, the data suggests that 40/60 PCL/PLA film supported significantly (p<0.05) higher levels of osteocalcin expression compared to TCPS. The rest of the polymer surfaces were equivalent to TCPS for both osteocalcin and AP mRNAs expression.

Conclusions

No major differences were observed with respect to cell attachment and proliferation between the different bioresorbable films or meshes tested following 6 days of incubation. Furthermore, the results indicate that differences between these materials were more obvious with respect to their differentiation characteristics. Cells cultured on 40/60 PCL/PLA film showed enhanced alkaline phosphatase activity and osteocalcin mRNA expression compared to other films and TCPS following 14 and 21 days of incubation, respectively.

References that may be referred to for a more complete understanding of this techniques include, M. A. Aronow, L. C. Gerstenfeld, T. A. Owen, M. S. Tassinari, G. S. Stein and J. B. Lian: "Factors that promote progressive development of the osteoblast phenotype in cultured fetal rat calvaria cells: *Journal of Cellular Physiology*, 143: 213–221 (1990) and Stein, G. S., Lian, J. B., and Owen, t. A. "Relationship of cell growth to the regulation of tissue-specific gene expression during osteoblast differentiation" FASEB, 4, 3111–3123 (1990).

Example 7
In vivo Study of Foam Blend in Swine Dermal Wound Healing Model

This example describes the results of implanting a 1 mm, 0.5 mm thickness foam tissue scaffolding in a swine full thickness excisional wound model. The foam tissue scaffold was made from a blend of 40/60 ε-caprolactone-co-lactide made as described in Example 8 and 35/65 ε-caprolactone-co-glycolide described in Example 9. These polymers were blended together and formed into 1 mm and 0.5 mm foams substantially as described in Example 3 (except that the cooling rate was 2.5° C. per minute and it was cooled only to −5° C.). Scanning electron micrographs of a 0.5 mm foam are presented in FIGS. 9A, 9B and 9C. The two thickness (0.5 mm and 1 mm) of foams were then tested in the wound excisional model with and without PDGF being provided. The resulting four different samples were then evaluated.

A blinded histologic evaluation was performed on 48 full thickness excisional wounds from four pigs (12 sites per animal) explanted at 8 days following wounding. The assessment was performed on H&E stained slides. During the histologic assessment, the following parameters were ranked/evaluated across the specimen set 1) cellular invasion of the matrix qualitative and quantitative assessments 2) infiltration of polymorphonuclear leukoctyes (PMNs) into the contact zone (ventral surface) of the matrix, 3) inflammation in the granulation tissue bed below (ventral to) the matrix, 4) reaction of the epidermis to the matrix, and 5) degree of fragmentation of the matrix.

Animal Husbandry:

The pigs were housed individually in cages (with a minimum floor area of 10-sq. ft.) and given identification. All pigs were assigned an individual animal number. A tag was placed on each individual animal cage listing the animal number, species/strain, surgical date, surgical technique and duration of the experiment and date of euthanasia. Each animal was clearly marked with an animal number on the base of the neck using a permanent marker.

The animal rooms were maintained at the range of 40 to 70% R.H. and 15 to 24° C. (59.0 to 75.2° F.). The animals were fed with a standard pig chow once per day, but were fasted overnight prior to any experimental procedure requiring anesthesia. Water was available ad libitum. A daily light:dark cycle of 12:12 hours was adopted.

Anesthesia:

On the initial day of the study, days of evaluation and the day of necropsy, the animals were restrained and anesthetized with either an intramuscular injection of Tiletamine HCl plus Zolazepam HCl (Telazol®, Fort Dodge Animal Health, Fort Dodge, Iowa 4 mg/ml) and Xylazine (Rompun®, Bayer Corporation, Agriculture Division, Animal Health, Shawnee Mission, Kans., 4mg/ml) or Isoflurane (AErrane® Fort Dodge Animal Health, Fort Dodge, Iowa) inhalatory anesthesia (5% vol.) administered via a nose cone. When the animal was in the surgical suite, it was maintained on Isoflurane (AErrane®) inhalatory anesthesia (2% vol.) administered via a nose cone. Food was available after recovery from each procedure.

Preparation of the Surgical Site:

One day prior to the surgical procedure, body weights were measured and the dorsal region of four pigs were clipped with an electric clipper equipped with a #40 surgical shaving blade. The shaved skin was then re-shaved closely with shaving cream and a razor and then rinsed. The shaved skin and entire animal (excluding the head) was then scrubbed with a surgical scrub brush-sponge with PCMX cleansing solution (Pharmaseal® Scrub Care® Baxter Healthcare Corporation, Pharmaseal Division, Valencia, Calif.) and then with HIBICLENS® chlorhexidine gluconate (available from COE Laboratories, Incorporated, Chicago, Ill.). The animal was wiped dry with a sterile towel. Sterile NU-GAUZE* gauze (from Johnson & Johnson Medical Incorporated, Arlington, Tex.) was placed over the dorsal surface of each animal and secured with WATERPROOF* tape (available from Johnson & Johnson Medical Incorporated, Arlington, Tex.). The entire torso region of the animal was then wrapped with Spandage™ elastic stretch bandage (available from MediTech International Corporation, Brooklyn, N.Y.) to maintain a clean surface overnight.

On the day of surgery, immediately prior to delivering the animal to the surgical suite, the dorsal skin was again scrubbed using a surgical scrub brush-sponge with PCMX cleansing solution (Pharmaseal® Scrub Care®), rinsed and wiped dry using a sterile towel, as performed on the previous day. The animals were placed prone on the surgical table and wiped with 70% alcohol and dried with sterile gauze. Using a sterile surgical marker (availabe from Codman a division of Johnson & Johnson Professional Incorporated, Raynham, Mass.) and an acetate template, marks were made on the dorsal skin according to the desired placement of each full-thickness wound.

Surgical Procedure:

Following anesthesia, under sterile conditions, twelve (12) full-thickness excisions (1.5×1.5 cm) per animal were made in two rows parallel to the spinal column on the left and right dorsal regions using a scalpel blade. A pair of scissors and/or scalpel blade was used to aid in the removal of skin and subcutaneous tissue. Bleeding was controlled by use of a sponge tamponade. Sufficient space was left between wounds to avoid wound-to-wound interference. The excised tissue was measured for thickness using a digital caliper.

Application of the Treatment and Dressing:

Each wound was submitted to a prepared, coded treatment regimen (study participants were blinded to all treatments). The primary dressing consisting of the sterile individual test article (1.5×1.5 cm soaked in sterile saline for 24 hours) was placed into the wound deficit in a predetermined scheme. The secondary dressing, a non-adherent, saline soaked, square of RELEASE* dressing (manufactured by Johnson & Johnson Medical Incorporated, Arlington, Tex.) was placed on top of the test article. A layer of BIOCLUSIVE* dressing (available from Johnson & Johnson Medical Incorporated, Arlington, Tex.) was sealed over the wounds to keep the wound moist and the dressing in place. Strips of Reston™ (3M Medical-Surgical Division, St. Paul, Minn.) polyurethane self-adhering foam were placed between the wounds to avoid cross-contamination due to wound fluid leakage, and to protect the wounds from damage and the dressing from displacement. A layer of NU-GAUZE* gauze was placed on top of the BIOCLUSIVE* dressing and Reston™ foam, and was secured with WATERPROOF* tape to protect the dressings. The animals were then dressed with Spandage™ elastic net to help keep the dressings in place.

The secondary dressings were removed and replaced daily with a fresh piece of saline soaked RELEASE* secondary dressing. The primary dressings (test articles) were not disturbed unless the unit was displaced or pushed out of the wound deficit.

Post-Operative Care and Clinical Observations:

After performing the procedures under anesthesia, the animals were returned to their cages and allowed to recover. The animals were given analgesics (buprenorphine hydrochloride [Buprenex Injectable, 0.01 mg/kg, im] sold by Reckitt & Colman Products, Hull, England) immediately post-surgery and the following day. After recovering from anesthesia, the pigs were observed for behavioral signs of discomfort or pain. No signs of pain were observed.

Each pig was observed twice daily after the day of surgery to determine its health status on the basis of general attitude and appearance, food consumption, fecal and urinary excretion and presence of abnormal discharges.

EUTHANASIA:

At the end of the study (8 days post-wounding), each animal was euthanized under anesthesia, with an intravenous injection of (1 ml/10 pounds body weight) Socumb™ pentobarbital sodium and phenytoin sodium euthanasia solution (sold by The Butler Company, Columbus, Ohio) via the marginal ear vein. Following euthanasia, the animals were observed to ensure that respiratory function had ceased and there was no palpable cardiac function. A stethoscope facilitated the assessment for the lack of cardiac function.

Tissue Harvesting:

Immediately following euthanasia, each wound, together with the underlying fat and a small portion of surrounding skin was excised. The tissue was placed in 10% neutral buffered formalin.

EVALUATIONS:

Visual Wound Assessment:

General observations were recorded for days 1–3, including displacement, wound reaction and physical characteristics of the scaffold. Detailed clinical evaluations were performed on days 4–8 post-wounding. Assessments were recorded as to the presence/absence (yes=1/no=0) and/or degree (given a score) of the following parameters:

Dressing Conditions: air exposed, displacement of test article, channeling, communication and moisture content of the RELEASE* secondary dressing(scored as: 4=moist, 3=moist/dry, 2=dry/moist, 1=dry).

Wound Bed Conditions: moisture content of test article (scored as: 4=moist, 3=moist/dry, 2=dry/moist, 1=dry), inflammation (scored as: 3=severe, 2=moderate, 1=slight, 0=none), reinjury (scored as: 3=severe, 2=moderate, 1=slight, 0=none), clots, folliculitis, infection, level of test article (scored as: 4=super raised, 3=raised, 2=even, 1=depressed), fibrin (scored as: 3=severe, 2=moderate, 1=slight, 0=none), and erythema. Color of the test article was also observed.

Tissue Processing:

Excised tissue samples were taken at day eight. The entire wound was harvested and placed into 10% neutral buffered formalin. The tissue was prepared for frozen sections. The tissue was trimmed and mounted onto the object holder with Tissue-Tek® OCT Compound (sold by Sakura Finetechnical Company, Limited, Tokyo, Japan) and quickly frozen. The specimens were sectioned on the cryostat at 10 μm and stained with a frozen H&E stain.

Histological Assessments (Day 8 post-wounding):

Histological evaluations for granulation tissue (area and length) and epithelialization were assessed using H&E stained specimens using a magnification of 20–40×. Granulation tissue height was determined by dividing the area by the length.

Histopathological evaluation of the tissue samples was assessed using the H&E stained specimens, they were first assessed under 100× to 400× magnification.

RESULTS

There was cellular invasion into the interstices of the dioxanone matrix in the majority of all test sites. In the majority of sites this invasion was true tissue ingrowth comprised of varying populations of fibroblasts, macrophages, macrophage giant cells, and endothelial-like cells, there also appeared to be capillary formation. Significant formation of dense fibrous connective tissue layer dorsal to the matrices essentially embedding the matrices in the tissue, was seen at several sites for the 0.5 mm foams with and without PDGF. The 1 mm matrices were either at the surface of the tissue bed or sloughed. Macrophage giant cell formation seemed to be greater in the 0.5 mm versus the 1 mm foam scaffolds. In sites where the 1 mm foam was being sloughed or partially separated from the underlying granulation tissue there was death of the invading cells forming masses of pyknotic cell debris.

Figure 11:
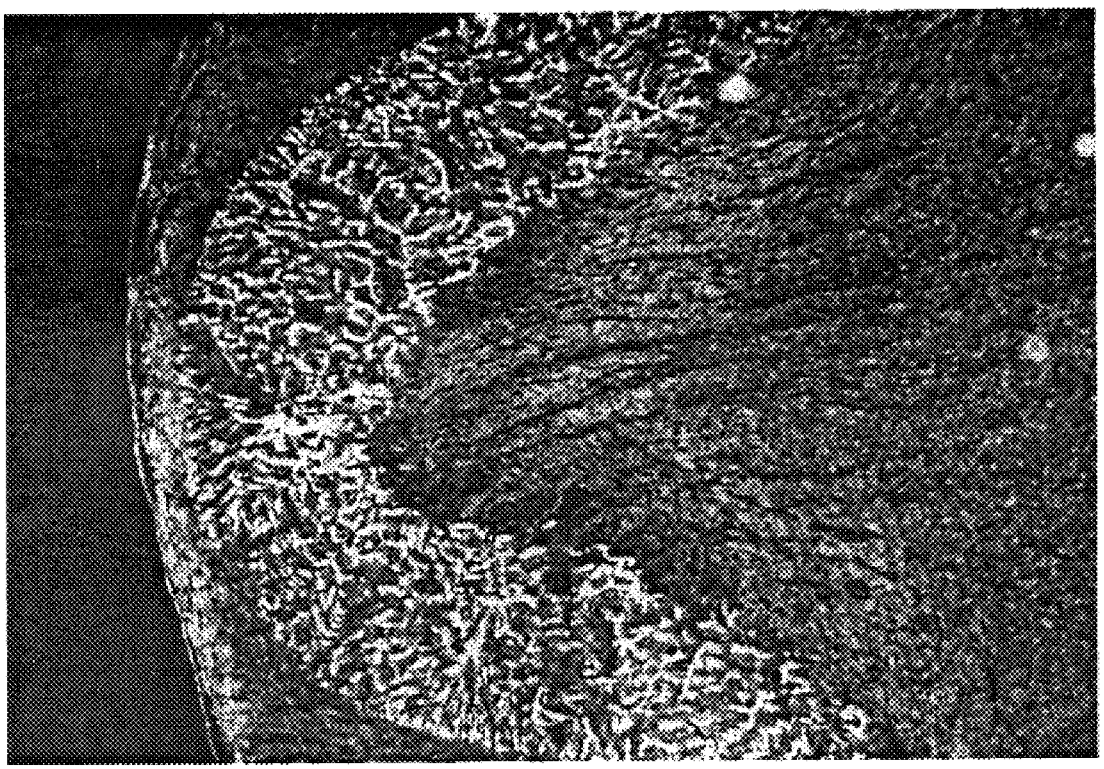
FIG. 11 is a 100× composite photomicrograph of a trichrome stained sample illustrating the cellular invasion of the foam shown in FIG. 9 which also contained PDGF, eight days after implantation in a swine model.

Complete incorporation of the matrix into the granulation tissue bed was seen at several sites for the 0.5 mm foam scaffoldings. FIGS. 10 and 11 illustrate the incorporation of these matrices into the granulation tissue bed. FIG. 10 is a dark filed 40× pictomicrograph of a trichrome stained tissue sample. FIG. 11 is a 100× composite photomicrograph of a trichrome stained sample illustrating the cellular invasion of a foam containing PDGF. Complete incorporation of the matrices into the granulation tissue bed is evident in both pictures. The dense fibrous tissue above the foam scaffolding is evident in both pictures. These results indicate the 0.5 mm foams will provide a suitable substrate for the growth of epidermal tissue.

Example 8
Synthesis of a Random Poly(ε-caprolactone-co-glycolide)

A random copolymer of ε-caprolactone-glycolide with a 35/65 molar composition was synthesized by ring opening polymerization reaction. The method of synthesis was essentially the method described in U.S. Pat. No. 5,468,253 in Example 6 (which is hereby incorporated herein by reference). The amount of diethylene glycol initiator added was adjusted to 1.15 mmole/mole of monomer to obtain the following characteristics of the dried polymer: The inherent viscosity (I.V.) of the copolymer was 1.59 dL/g in hexafluoroisopropanol at 25° C. The molar ratio of PCL/PGA was found to be 35.5/64.5 by proton NMR with about 0.5% residual monomer. The glass transition (Tg) and the melting points (Tm) of the copolymer were found to be −1° C., 60° C. and 126° C. respectively, by DSC.

Example 9
Synthesis of 40:60 Poly(ε-caprolactone-co-L-lactide) by Sequential Addition In the glove box, 100 µL (33 µmol) of a 0.33 M stannous octoate solution in toluene, 115 µL (1.2 mmol) of diethylene glycol, 24.6 grams (170 mmol) of L-lactide, and 45.7 grams (400 mmol) of ε-caprolactone were transferred into a silanized, flame dried, two neck, 250 mL round bottom flask equipped with a stainless steel mechanical stirrer and a nitrogen gas blanket. The reaction flask was placed in an oil bath already set at 190° C. and held there. Meanwhile, in the glove box, 62.0 grams (430 mmol) L-lactide were transferred into a flame dried, pressure equalizing addition funnel. The funnel was wrapped with heat tape and attached to the second neck of the reaction flask. After 6 hours at 190° C., the molten L-lactide was added to the reaction flask over 5 minutes. The reaction was continued overnight for a total reaction time of 24 hours at 190° C. The reaction was allowed to cool to room temperature overnight. The copolymer was isolated from the reaction flask by freezing in liquid nitrogen and breaking the glass. Any remaining glass fragments were removed from the copolymer using a bench grinder. The copolymer was again frozen with liquid nitrogen and broken off the mechanical stirring paddle. The copolymer was ground into a tared glass jar using a Wiley Mill and allowed to warm to room temperature in a vacuum oven overnight. 103.13 grams of 40:60 poly(ε-caprolactone-co-L-lactide) were added to a tared aluminum pan and then devolitilized under vacuum at 110° C. for 54 hours. 98.7 grams (95.7% by weight) of copolymer were recovered after devolitilization. The inherent viscosity was measured and found to be 1.1 dL/g in $CHCl_3$ at 25° C. (c=0.1 g/dL). FTIR (cast film from $CHCl_3$ onto KBr window, $cm^{-1}$): 2993, 2944, 2868, 1759, 1456, 1383, 1362, 1184, 1132, 1094, 870, and 756. $^1$H NMR (400 MHz, HFAD/Benzene, ppm): δ1.25, 2 broad lines (e); 1.35, 2 lines (f); 1.42, 3 lines; 1.55, 2 lines; 2.22, 3 lines ; 2.35, 4 broad lines; 4.01, 3 lines; 4.05, 3 lines; 4.2, quartet; 5.05, 3 broad lines; 5.15, 4 lines. Polymer composition by $^1$H NMR: 41.8% PCL, 57.5% PLA, 0.8% L-lactide, <0.1% ε-caprolactone. DSC (20° C./min, first heat): $T_m$=154.8° C., $\Delta H_m$=18.3 J/g. GPC (molecular weights determined in THF using poly(methyl methacrylate) standards, daltons) : $M_w$=160,000, $M_n$=101,000, PDI=1.6.

Example 10
Synthesis of 95/15 PLA/PCL Copolymer

In the glove box, 170 µL (1.8 mmol) of diethylene glycol, 350 µL (115 µmol) of a 0.33 M stannous octoate solution in toluene, 17.1 grams (150 mmol) of ε-caprolactone, and 410.4 grams (2.85 mol) of L-lactide were placed into a silanized, flame dried, 1000 mL round bottom equipped with a stainless steel mechanical stirrer and vacuum take off connector in order to maintain a dry nitrogen gas blanket. The reaction flask was placed in an oil bath already heated to 185° C. and then held there for 3 hours. The flask was removed from the oil bath and allowed to cool down to room temperature. The polymer was isolated by wrapping the flask with aluminum foil, freezing it in liquid nitrogen, and then grinding away any adhered glass to the polymer. The copolymer was then ground in a Wiley mill. The ground polymer was vacuum dried at 80° C. for 24 hours. 302 grams of copolymer were collected. The inherent viscosity was 2.1 dL/g in chloroform [25° C., c=0.1 g/dL]. The copolymer composition was measured by proton NMR spectroscopy and found to be 97.2 mole percent PLA and 2.8 mole percent PCL. No residual monomer was detected.

Example 11
Synthesis of 60/40 PLA/PCL Hybrid foam/microfibrous fabric structure Step A. Preparing 14% wt./wt. Homogenous solution of 60/40 PLA/PCL in trichloroethane A 14% wt./wt. Polymer solution is prepared by dissolving 14 parts 60/40 PLA/PCL (I.V.=1.34 dl/g) with 86 parts of the solvent trichloroethane (TCE). The solution is prepared in a flask with a magnetic stir bar. For the copolymer to dissolve completely, it is recommended that the mixture stir overnight at 60 degrees C.

Step B. Electrostatic spinning

The electrostatic spinner was used for this experiment. Spellman High Voltage DC Supply (Model No.: RHR30PN30, Spellman High Voltage Electronics Corporation, Hauppauge, N.Y., USA) was used as high voltage source. Applied voltage and the speed of mandrel were controlled by the Labview computer software. Distance between the spinneret was mechanically controlled.

A flat sheet of lyophilized 60/40 PLA/PCL foam, prepared as described in Example 1, was rolled into a cylinder. The ends were secured together with several drops of trichloroethane (TCE), the solvent used in spinning. The foam tube was mounted onto a rotating conductive mandrel that was grounded. The ends of the mandrel not covered by the foam substrate were masked with an insulating tape to prevent the attraction of the microfibers to the ends. The solution was placed into a spinneret and high voltage was applied to the polymer solution. This experiment was performed at ambient temperature and humidity.

The operating conditions during spinning were as follows:

| | |
|---|---|
| Mandrel voltage | 16,000 V |
| Mandrel speed | 100 rpm |
| Spinneret to mandrel distance | 10 cm |
| Temperature | room temperature |
| Humidity | ambient humidity |

A layer of approximately 200 um in thickness was deposited on the outer surface of the tube

Example 12
Chondrocytes cultured in an encapsulated hybrid foam/fabric structure demonstrating the limitation of cell migration Step A. Preparation of hybrid 60/40 PLA/PCL foam/microfibrous fabric scaffolds Lyophilized foams made from 60/40 PLA/PCL as described in Example 1 were used as substrates during the electrostatic spinning of 60/40 PLA/PCL in trichloroethane, as described in detail in Example 11.

Step B. Chrondrocyte seeding into the hybrid 60/40 PLA/PCL foam/microfibrous fabric scaffold Chondrocytes isolated from bovine shoulders were cultured in Dulbecco's modified Eagle medium (high glucose) supplemented with 10% fetal calf serum, 10 mM HEPES, 0.1 mM nonessential amino acids, 20 ug/ml streptomycin, and 0.25 ug/ml amphotericin B.

3-D Transmigration Assay:

This assay is based on cell-populated contracted collagen lattice with a biodegradable polymer scaffold implanted at the center of the collagen gel. The dermal equivalents (collagen lattice) were fabricated from a mixture of the following: 8 ml of chondrocyte media, 2 ml of neutralizing medium (DMEM/10% FBS containing 0.1 N NaOH, prepared prior to use), 4 ml of rat tail type I collagen (3.99 mg/ml) obtained from Collaborative Biomedical Products, and 2 ml of chondrocyte suspension in chondrocyte medium. The above cell/collagen mixture was distributed (2 ml) to each well of a 24-well hydrogel-coated plate (Costar, Cat # 3473). The final cell concentration was $6\times10^6$ cells/ml and the collagen concentration was 1 mg/ml. The collagen gels was allowed to polymerize at 37° C. for 1 h. Following gel polymerization, 1.5 ml of chondrocyte growth medium was applied into each well. The medium was changed every other day. After 7 days of contraction, wounds at 5 mm in diameter were made throughout the thickness of the collagen lattice using a disposable 5 mm biopsy punch. Tested scaffolds, approximately 5 mm in diameter and 2 mm thick, supplied in a wet form, were implanted into a center of the wounded collagen lattice. To assure that the scaffold would not be pushed out from the wound bed during contraction of the collagen lattice, 50 $\mu$l of acellular collagen was placed on the top of each construct. Constructs were cultivated in chondrocyte media with medium being changed in a 2-day interval. The contracted gels containing the scaffold were cultured either statically in ultra low cluster dishes or in the bioreactor and collected after 3 weeks.

Step C. Cell characterization within the scaffolds

Histology was performed on the scaffolds invaded by cells. Scaffolds were fixed in 10% buffered formalin and were either embedded in paraffin and sectioned (hybrid foam/microfibrous fabric scaffolds) or cryosectioned (control foam scaffolds). Sections were stained with Hematoxylin/eosin (H/E, cell number and morphology), Safranin O (SO; sulfated GAGs) and Trichrome (collagen). Quantitation of cell invasion into these scaffolds was determined by image analysis. Analysis of Variance with Tukey post hoc tests were performed on the data.

Experimental Results

Quantitative evaluation of H/E sections of constructs cultured for 3 weeks revealed that chondrocytes invaded both scaffolds. Cell invasion into the hybrid foam/microfibrous fabric scaffolds, cultured in the bioreactor, was significantly higher (P<0.05) than into 40/60 PCL/PLA foam scaffolds. Also in the statically maintained cultures the cell invasion into the hybrid foam/microfibrous fabric scaffolds was significantly (P<0.05) higher than into 40/60 PCL/PLA foam scaffolds.

|  | 40/60 PCL/PLA foam scaffolds | Hybrid foam/microfibrous fabric scaffolds |
|---|---|---|
| Cell invasion cells/mm2 (3 weeks) Static Cell Culture Bioreactor Cell Culture | 50 140 | 80 200 |

Hybrid foam/microfibrous fabric scaffolds exhibited the highest cell density. We hypothesize that cell-cell interactions, presumably higher in the case of hybrid foam/microfibrous fabric scaffolds as compared to the other scaffold, may have contributed to preferential chondrocyte proliferation and differentiated functions on hybrid foam/microfibrous fabric scaffolds. The cell-cell interactions are postulated to play a critical role in the maintenance of chondrocyte phenotype. Chondrocytes are known to dedifferentiate when expanded in cell monolayer. When cultured in monolayer at high cell density chondrocytes maintain their phenotype as indicated by the expression of type II collagen and aggrecan.

By 6 weeks, 40/60 PCL/PLA foam scaffolds, showed cartilage-like morphology/properties localized mainly within the capsule around the construct. In contrast, in hybrid foam/microfibrous fabric scaffolds,the capsule was very thin and the cell morphology within the constructs was cartilage-like and a more uniform distribution of cells was observed.

We claim:

1. A biocompatible composite comprising a first biocompatible filamentous layer attached to a second biocompatible foam layer wherein the biocompatible foam is selected from the group consisting of gradient foams and channeled foams; wherein the gradient foam has a first location and a second location wherein the biocompatible gradient foam has a substantially continuous transition in at least one characteristic selected from the group consisting of composition, stiffness, flexibility, bioabsorption rate and pore architecture from the first location to the second location of said biocompatible gradient foam and the channeled foam has a first surface and a second surface with channels therein.

2. The biocompatible composite of claim 1 wherein the biocompatible foam is bioabsorbable.

3. The biocompatible composite of claim 1 wherein the biocompatible filamentous layer is bioabsorbable.

4. The biocompatible composite of claim 1 wherein the biocompatible composite is made from a bioabsorbable polymer selected from the group consisting of aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amine groups poly(anhydrides), polyphosphazenes, biopolymers and blends thereof.

5. The biocompatible composite of claim 4 wherein the bioabsorable polymer is an aliphatic polyester.

6. The biocompatible composite of claim 5 wherein the aliphatic polyester is selected from the group consisting of homopolymers and copolymers of lactide, lactic acid, glycolide, glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, E-decalactone, hydroxybutyrate, hydroxyvalerate, 1,4-dioxepan-2-one, 1,5, 8, 12-tetraoxacyclotetradecane-7,14-dione), 1, 5-dioxepan-2-one, 6,6-dimethyl-1, 4-dioxan-2-one and polymer blends thereof.

7. The biocompatible composite of claim 5 wherein the aliphatic polyester is an elastomer.

8. The biocompatible composite of claim 7 wherein the elastomer is selected from the group consisting of copolymers of ε-caprolactone and glycolide; copolymers of ε-caprolactone and (L)lactide, copolymers of p-dioxanone (1,4-dioxan-2-one) and (L)lactide, copolymers of ε-caprolactone and p-dioxanone, copolymers of p-dioxanone and trimethylene carbonate, copolymers of trimethylene carbonate and glycolide, copolymer of trimethylene carbonate and (L)lactide and blends thereof.

9. The biocompatible composite of claim 5 wherein additionally present as a constituent of the biocompatible foam is a second aliphatic polyester.

10. The biocompatible composite of claim 5 wherein additionally present as a constituent of the biocompatible filamentous layer is a second aliphatic polyester.

11. The biocompatible composite of claim 4 wherein the biocompatible gradient foam has a substantially continuous transition in composition from the first location to the second location.

12. The biocompatible composite of claim 11 wherein the biocompatible gradient foam has a substantially continuous transition in composition from a first ratio of at least two different aliphatic polyesters to a second ratio of said at least two different aliphatic polyesters from the first surface to the second surface.

13. The biocompatible composite of claim 4 wherein the biocompatible gradient foam has a substantially continuous transition in stiffness from the first location to the second location.

14. The biocompatible composite of claim 4 wherein the biocompatible gradient foam has a substantially continuous transition in bioabsorption rate from the first location to the second location.

15. The biocompatible composite of claim 4 wherein the biocompatible gradient foam has a substantially continuous transition in flexibility from the first location to the second location.

16. The biocompatible composite of claim 4 wherein the biocompatible gradient foam has a substantially continuous transition in architecture from the first location to the second location.

17. The biocompatible composite of claim 16 wherein the biocompatible gradient foam has a substantially continuous transition in architecture from a substantially spherical pore shape to a columnar pore shape from the first location to the second location.

18. The biocompatible composite of claim 16 wherein the substantially spherical pore's size is from about 30 µm to about 150 µm.

19. The biocompatible composite of claim 16 wherein the columnar pore's diameter is from about 100 µm to about 400 µm with a length to diameter ratio of at least 2.

20. The biocompatible composite of claim 1 wherein also present in the biocompatible composite is a therapeutic agent.

21. The biocompatible composite of claim 1 wherein additionally present is an agent is selected from the group consisting of antiinfectives, hormones, analgesics, anti-inflammatory agents, growth factors, chemotherapeutic agents, anti-rejection agents prostaglandins, RDG peptides and combinations thereof.

22. The biocompatible composite of claim 21 wherein the growth factor is selected from the group consisting of bone morphogenic proteins, bone morphogenic-like proteins, epidermal growth factor, fibroblast growth factors, platelet derived growth factor, insulin like growth factor, transforming growth factors, vascular endothelial growth factor and combinations thereof.

23. The biocompatible composite of claim 1 wherein the biocompatible compatible foam is filled with a biocompatible material selected from the group consisting of bioabsorbable synthetic polymers, biocompatible, bioabsorbable biopolymers, biocompatible ceramic materials and combinations thereof.

24. The biocompatible composites of claim 1 wherein the channeled foam has channels with an average length of at least 200 µm.

25. The biocompatible composites of claim 24 wherein the channels extend substantially from said first surface to said second surface.

26. The biocompatible composite of claim 1 wherein the biocompatible foam has interconnected pores formed from a composition containing in the range of from about 30 weight percent to about 99 weight percent ε-caprolactone repeating units.

27. The biocompatible composite of claim 26 wherein the ε-caprolactone repeating units are copolymerized with a comonomer selected from the group consisting of lactide, lactic acid, glycolide, glycolic acid), p-dioxanone (1,4-dioxan-2-one), trimethylene carbonate (1, 3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one, 1,5, 8,12-tetraoxacyclotetradecane-7,14-dione), 1,5-dioxepan-2-one, 6,6-dimethyl-1,4-dioxan-2-one and polymer blends thereof.

28. The biocompatible composite of claim 26 having a first location and a second location wherein the biocompatible foam has a substantially continuous transition in at least one characteristic selected from the group consisting of composition, stiffness, flexibility, bioabsorption rate and pore architecture from the first location to the second location of said biocompatible foam.

29. The biocompatible composite of claim 26 wherein the interconnecting pores have a pore size in the range from about 10 µm to about 200 µm.

30. The biocompatible composite of claim 26 wherein the biocompatible foam has a porosity of in the range of from about 20 to about 98 percent.

31. The biocompatible composite of claim 26 wherein the biocompatible foam has channels.

32. The biocompatible composites of claim 31 wherein the channels have an average length of at least 200 µm.

33. The biocompatible composite of claim 26 wherein the substantially spherical pore's size is from about 30 µm to about 150 µm.

34. The biocompatible composite of claim 26 wherein the columnar pore's diameter is from about 30 µm to about 400 µm with a length to diameter ratio of at least 2.

35. The biocompatible composite of claim 26 wherein also present in the biocompatible foam is a therapeutic agent.

36. The biocompatible composite of claim 1 wherein the biocompatible foam is formed with an insert within the biocompatible foam.

37. The biocompatible composite of claim 36 wherein the insert is selected from the group consisting of films, scrims, woven textiles, knitted textiles, braided textiles, orthopedic implants, tubes and combinations thereof.

38. The biocompatible composite of claim 1 wherein the biocompatible composite is formed into a three-dimensional shaped structure.

39. The biocompatible composite of claim 38 wherein the three-dimensional shaped structure is selected from the group consisting of tubular shapes, branched tubular shapes, spherical shapes, hemispherical shapes, three-dimensional polygonal shapes, ellipsoidal shapes, toroidal shapes, conical shapes, frusta conical shapes, pyramidal shapes, both as solid and hollow constructs and combination thereof.

* * * * *